United States Patent [19]

Kitazawa et al.

[11] Patent Number: 5,173,554
[45] Date of Patent: Dec. 22, 1992

[54] GLYCOSIDE DERIVATIVES, POLYMERS CONTAINING GLYCOSIDE DERIVATIVES, PROCESS FOR THEIR PREPARATION, AND USE OF SAID POLYMERS

[75] Inventors: Sadaya Kitazawa, Himeji; Masakazu Okumura, Kakogawa; Masaki Kojima, Himeji; Keisuke Kinomura, Kakogawa; Toshiyuki Sakakibara, Kobe, all of Japan

[73] Assignee: Nippon Fine Chemical Co., Ltd., Osaka, Japan

[21] Appl. No.: 886,358

[22] Filed: May 21, 1992

Related U.S. Application Data

[62] Division of Ser. No. 499,459, Jun. 26, 1990.

[30] Foreign Application Priority Data

Oct. 27, 1988 [JP] Japan .................. 63-272168
Dec. 29, 1988 [JP] Japan .................. 63-332116

[51] Int. Cl.$^5$ ................ C08F 24/00; C07H 15/04
[52] U.S. Cl. ................ 526/238.2; 536/116
[58] Field of Search .......... 526/238.2, 238.21, 238.22, 526/238.23

[56] References Cited

U.S. PATENT DOCUMENTS 3,989,656 11/1976 Kamiya et al. .................. 526/238.2

FOREIGN PATENT DOCUMENTS 59-45306 3/1984 Japan .

Primary Examiner—Joseph L. Schofer
Assistant Examiner—Wu C. Cheng
Attorney, Agent, or Firm—Larson and Taylor

[57] ABSTRACT

The present invention provides a glycoside derivative represented by the formula

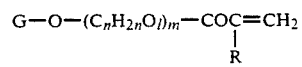

wherein G—O— is a saccharide residue having no protective group, R is a hydrogen atom or a methyl group, m is 1 or 2, n is an integer of 1 to 4, and l is an integer of 1 or more provided that $1 \leq n$; a polymer containing the glycoside derivative; a process for their preparation, and the use of the polymers.

8 Claims, 9 Drawing Sheets

GLYCOSIDE DERIVATIVES, POLYMERS CONTAINING GLYCOSIDE DERIVATIVES, PROCESS FOR THEIR PREPARATION, AND USE OF SAID POLYMERS

This is a division of application Ser. No. 07/499,459 filed Jun 26, 1990, which is now pending.

1. Field of the Invention

The present invention relates to glycoside derivatives, polymers containing the glycoside derivatives, a process for their preparation and the use of said polymers.

2. Prior Art

Polymers having saccharide residues at side chains are increasingly used for various applications utilizing their hydrophilic property and compatibility with organisms, for example, as medical materials including those compatible with blood, surface-treating agents, etc.

The heretofore proposed polymers having saccharide residues at side chains are generally classified into the following two types.

(i) Polymers having saccharide residues obtained by the reaction of known polymers with sugar derivatives.

For example, Japanese Unexamined Patent Publications No. 106802/1985 and No. 192704/1985 disclose the preparation of such polymers by reacting a hydroxymethylated polystyrene with a sugar having hydroxyl groups protected with protective groups such as acetyl groups, halogen atoms or the like, followed by saponification of protective groups of the sugar with an alkali. These polymers, however, have a poor hydrophilic property and a low compatibility with organisms because the protective groups on saccharide residues are not completely removed and the saccharide residues are not uniformly added to the polymers. Further this process can not regulate as desired the amount of the sugar to be added and entails difficulties in removing the reagent used and purifying the polymer thus formed.

(ii) Polymers formed by reacting a vinyl monomer with a saccharide having hydroxyl groups protected with protective groups such as acetyl groups, isopropylidene groups or the like and removing the protective groups after polymerization For example, U.S. Pat. No. 3,225,012 discloses a polymer represented by the formula

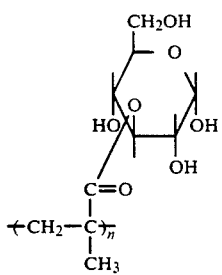

the polymer being one prepared by polymerizing 1,2:5,6-di-O-isopropylidene-3-O-methacryloy-D-glucose and removing the isopropylidene groups from the glucose by acid hydrolysis.

U.S. Pat. No. 3,356,652 describes a polymer having structural units represented by the formula

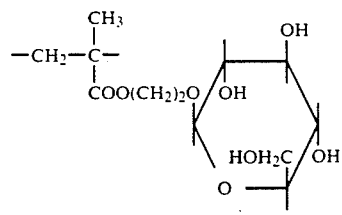

As further example, Japanese Examined Patent Publication No. 42641/1982 discloses a homopolymer represented by the formula

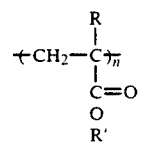

wherein R is a hydrogen atom or a methyl group, R' is a sugar residue attached with the acyl linkage at the 1-position and n is 10 to 1000, the homopolymer being one formed from a monomer which is a sugar derivative having a monosaccharide or disaccharide and an acrylate or methacrylate directly attached to each other with the glycoside linkage.

These publications set forth techniques intended to remove the protective groups with an alkali or acid from the hydroxyl groups of the sugar in the obtained polymer. However, the currently available art can not completely remove the protective groups in polymers. Actually U.S. Pat. No. 3,356,652 teaches that it is impossible to completely remove the acetyl groups in a copolymer containing a hydrophobic monomer. Thus the obtained polymer contains a substantial number of protected hydroxyl groups and is unsatisfactory in hydrophilic property and compatibility with organisms. The treatment of polymers with an alkali or acid impairs the properties of the resulting polymer. Moreover such methods necessitate the neutralization of alkali or acid after removal of protective groups from hydroxyl groups and the washing by water of the salt resulting from neutralization for elimination. The removal of protective groups renders the polymer hydrophilic to give an aqueous viscous solution or water-swollen gel, resulting in incomplete neutralization and desalting. Consequently the polymers formed by the methods are not suitable for use as medical materials.

As described above, polymers with saccharide residues at side chains having no protective group have not been heretofore obtained.

DISCLOSURE OF THE INVENTION

It is an object of the present invention to provide a monomeric compound useful for synthesis of a polymer having as side chains saccharide residues free of the protective group and a process for preparing the same.

It is another object of the invention to provide a polymer having as side chains saccharide residues free of the protective group and a process for preparing the same.

According to the invention, there are provided glycoside derivatives, a polymer containing said glycoside derivatives and a process for their preparation, as described below.

(1) A glycoside derivative represented by the formula

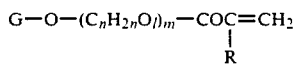

wherein G—O— is a sugar residue free of the protective group, R is a hydrogen atom or a methyl group, m is 1 or 2, n is an integer of 1 to 4, and l is an integer of 1 or more provided that $l \leq n$.

The glycoside derivative (1) is a novel compound undisclosed in literature and useful as a monomer for synthesis of a polymer with sugar residues at side chains having no protective group.

Figure 1:
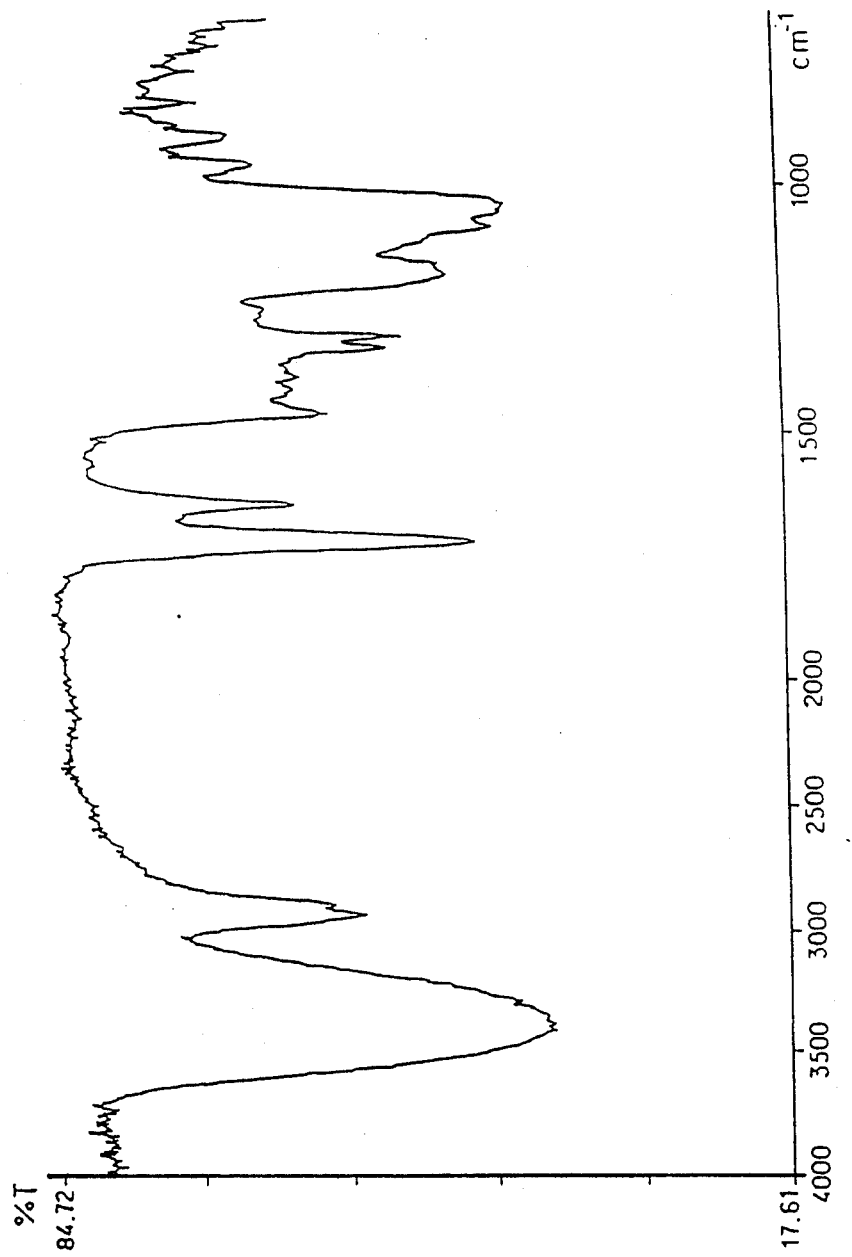
FIG. 1 shows the IR spectrum of galactosyloxyethyl acrylate.

The glycoside derivative (1) is a novel compound undisclosed in literature and useful as a monomer for synthesis of a polymer with sugar residues at side chains having no protective group.

(2) A polymer containing a glycoside derivative, the polymer having at least one of the following repeated units (I) represented by the formula

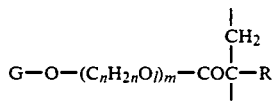

wherein G—O—, R, m, n, and l are as defined above.

The polymer (2) containing the glycoside derivative is a novel polymer undisclosed in literature. In the polymer, the sugar residues free of the protective group, namely having hydroxyl groups all remaining free, are attached to the main chain with the glycoside linkage. Since glycoside linkages exist in organisms or in nature, the foregoing polymer is compatible with organisms. Further, because the hydroxyl groups of sugar residues in the polymer are unprotected and free, the polymer is excellent in the hydrophilic property and compatibility with blood. The polymer has another advantage of high moldability. With these characteristics, the polymer finds various applications as blood-compatible materials or like medical materials, coating materials for forming a non-fogging film on a transparent material such as plastics, glass or the like, water-absorbing resin materials, etc.

The term "saccharide residue" used herein refers to a saccharide residue wherein a hydrogen atom is removed from the hydroxyl group attached to the anomeric carbon atom of saccharide. More specifically they are the saccharide residues of monosaccharide or oligosaccharide having about 1 to about 10, preferably about 1 to about 5, more preferably about 1 to 3, sugar units. Examples of typical monosaccharides are glucose, mannose, galactose, glucosamine, mannosamine, galactosamine and like hexoses, arabinose, xylose, ribose and like pentoses, etc. Examples of specific oligosaccharides are maltose, lactose, trehalose, cellobiose, isomaltose, gentiobiose, melibiose, laminaribiose, chitobiose, xylobiose, mannobiose, sophorose and like disaccharides, maltotriose, isomaltotriose, maltotetraose, maltopentaose, mannotriose, manninotriose, etc.

The term "lower alkyl group" used herein is intended to denote a straight or branched chain alkyl group having about 1 to about 4 carbon atoms such as methyl, ethyl, propyl, isopropyl, butyl, tert-butyl, isobutyl, etc.

The glycoside derivative (1) of the present invention can be prepared by reacting an alkyl glycoside represented by the formula

wherein G—O— is as defined above and $R^1$ is a lower alkyl group with an acrylate or methacrylate represented by the formula

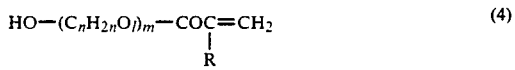

wherein R, m, n and l are as defined above in the presence of a heteropoly acid and a polymerization inhibitor. The reaction can be conducted in the absence or the presence of a solvent.

The alkyl glycosides of the formula (3) useful as the starting compound are not specifically limited and include those prepared by conventional methods such as the Koenigs-Knorr method, the Fischer's alcoholysis method, the method proposed by us (Japanese Unexamined Patent Publication No. 84637/1988, "Synthesis of Glycoside by Heteropoly acid, (1) Synthesis of O-Alkylglycoside" reported in the 56th Spring Annual Meeting, 1988, Japan Chemical Society), etc. Commercially available glycosides may be used in the invention. Among them, preferable are alkyl glycosides in which the alkyl moiety is a straight or branched chain alkyl group having about 1 to about 6 carbon atoms, preferably about 1 to about 4 carbon atoms, such as methyl glucoside, methyl β-D-galactoside, methyl D-maltoside, methyl β-D-mannoside, methyl β-D-xyloside, methyl D-maltoside, methyl β-D-lactoside, ethyl glucoside, ethyl galactoside, ethyl mannoside, ethyl xyloside, propyl glucoside, isopropyl glucoside, butyl glucoside, butyl galactoside, butyl xyloside, butyl mannoside, etc. These alkyl glycosides of the formula (3) are usable singly or at least two of them can be used in mixture.

The other starting material, i.e. the acrylate or methacrylate of the formula (4), is not specifically limited and can be any of conventional ones including 2-hydroxyethyl acrylate, 2-hydroxypropyl acrylate, 2- hydroxyethyl methacrylate, 2-hydroxypropyl methacrylate, diethyleneglycol acrylate, diethyleneglycol methacrylate, glycerin acrylate, glycerin methacrylate, pentaerythritol acrylate, pentaerythritol methacrylate, etc.

The amount of the acrylate or methacrylate of the formula (4) used is not specifically limited and is about 2 to about 10 moles, preferably about 4 to about 6 moles, per mole of the alkylglycoside of the formula (3).

The heteropoly acid is not specifically limited. Preferred heteropoly acids are phosphomolybdic acid, silicomolybdic acid, phosphotungstic acid, silicotungstic acid, etc. These heteropoly acids are useable singly or at least two of them can be used in mixture. The amount of the heteropoly acid used is not specifically limited and is about 1 to about 20% by weight, preferably about 5 to about 10% by weight, based on the alkyl glycoside of the formula (3) used.

The polymerization inhibitor is not specifically limited and can be any of conventional ones. Examples of useful inhibitors are hydroquinone monomethyl ether, hydroquinone monoethyl ether, butylhydroxytoluene, butylcatechol, benzoquinone, nitrobenzene, cupric chloride, ferric chloride, etc. These inhibitors are usable singly or at least two of them can be used in mixture. The amount of the inhibitor used is not specifically limited, and is about 0.5 to about 5% by weight, preferably about 1 to about 2% by weight, based on the acrylate or methacrylate of the formula (4).

Useful solvents are those which affect the reaction in no way. Examples of such solvents are halogenated hydrocarbons such as dichloromethane, chloroform, 1,2-dichloroethane, 1,1,1-trichloroethane, 1,1,2-trichloroethane, 1,1,2,2-tetrachloroethane, chlorobenzene and the like; aromatic hydrocarbons such as benzene, toluene, xylene and the like; and ethers such as ethyl ether, isopropyl ether, ethyleneglycol dimethyl ether, ethyleneglycol diethyl ether, diethyleneglycol dimethyl ether, dioxane, tetrahydrofuran and the like. These solvents are usable singly or at least two of them can be used in mixture.

The reaction temperature and the reaction time are not specifically limited. The reaction temperature is in the range of about 50° to about 150° C., preferably about 80° to about 120° C. The reaction time is in the range of about 1 to 3 hours.

The glycoside derivative (1) can be prepared also by reacting a sugar having no protective group with an ester of acrylic or methacrylic acid in the presence of an acid catalyst and a polymerization inhibitor while feeding oxygen to the reaction system. This process gives the contemplated glycoside derivative (1) in a high yield using an easily available sugar having no protective group without use of an alkyl glycoside which is relatively difficult to synthesize or obtain.

Among sugars having no protective group, monosaccharides or oligosaccharides having about 1 to about 10, preferably about 1 to about 5, more preferably about 1 to about 3, sugar units as exemplified above are usable without specific limitation.

Esters of acrylic or methacrylic acids useful in the invention are those of the formula (4). The amount of such ester used is not specifically limited but usually in the range of about 2 to about 20 moles, preferably about 4 to about 10 moles, per mole of the sugar having no protective group.

The acid catalyst is not specifically limited and can be any of conventional ones including inorganic acids such as sulfuric acid, chlorosulfonic acid, hydrochloric acid, hydrobromic acid, perchloric acid, nitric acid, phosphorus trichloride, phosphorus pentachloride, phosphorus oxychloride, stannic chloride, aluminum chloride, iron chloride, zinc chloride and the like, organosulfonic acids such as toluenesulfonic acid, laurylsulfonic acid, methanesulfonic acid, alkylbenzenesulfonic acid, trifluoromethanesulfonic acid and the like, and esters of sulfuric acids such as lauryl sulfate, methyl sulfate, ethyl sulfate and the like. Strongly acidic ion-exchange resins (acid type), NAFION and like acidic polymers are also usable as the acid catalyst. Preferred acid catalysts are those which can not be readily reduced. The acid catalysts are usable singly or at least two of them can be used in mixture. The amount of the acid catalyst used is not specifically limited but usually in the range of about 0.001 to about 2.0% by weight, preferably about 0.005 to about 0.1% by weight, based on the ester of acrylic or methacrylic acid used.

The polymerization inhibitors as exemplified above can be used in this reaction and the amount of the inhibitor is approximately the same as described above.

The methods for feed of oxygen to the reaction system are not specifically limited. The feed of oxygen may be carried out, for example, by blowing oxygen or an oxygen-containing gas such as air into the reaction mixture. The amount of oxygen to be blown is not specifically limited and can be suitably determined according to the progress of the reaction. For example, about 30 to about 60 l/h of oxygen is fed to about 40 to about 50 l of the total reaction mixture.

The above reaction is conducted usually in the absence of a solvent at a temperature of about 80° to about 130° C., preferably about 100° to about 120° C. and is completed in about 2 to about 5 hours. It is preferred to conduct the reaction with stirring because the reaction more advantageously proceeds with an increase in the area of contact between the reaction mixture and oxygen.

The glycoside derivative (1) prepared by the above reaction can be purified by common purification methods such as silica gel chromatography, extraction or the like.

The polymer 2) of the invention includes homopolymers having the repeated units (I), copolymers having at least two different repeated units (I) and copolymers having the repeated units (I) and repeated units copolymerizable therewith. Olefin-type repeated units are usable as the copolymerizable units. More specific examples thereof are repeated units represented by the formula (II)

(II)

wherein $R^2$, $R^3$ and $R^4$ are the same or different and each represent a hydrogen atom or a lower alkyl group, and $R^5$ is a group

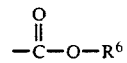

(wherein $R^6$ is a hydrogen atom, an alkyl group, a hydroxyalkyl group, a cycloalkyl group, an aminoalkyl group, a dialkylaminoalkyl group, a glycidyl group, a tetrahydrofuranyl group, a benzyl group, a group —(CH$_2$CH$_2$O)$_a$CH$_2$CH$_2$OH (wherein a is an integer of 1 to 10), a group

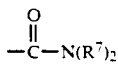

(wherein R$^7$ is a hydrogen atom or a lower alkyl group, provided that two groups R$^7$ are the same or different), a cyano group, a hydroxy group, a group

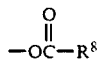

(wherein R$^8$ is a lower alkyl group), a phenyl group which may have at least one substituent selected from the group consisting of chlorine atom, lower alkyl group, cyano group, amino group, hydroxy group and lower alkoxy group, a pyridyl group optionally substituted with a lower alkyl group, a 2-oxopyrrolyl group optionally substituted with an alkyl group, or a carbazole group.

Examples of the alkyl group represented by R$^6$ in the formula (II) are straight chain or branched chain alkyl groups having about 1 to about 22 carbon atoms, preferably about 1 to about 10 carbon atoms such as methyl, ethyl, propyl, isopropyl, butyl, tert-butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and the like.

Examples of the hydroxyalkyl group are hydroxyalkyl groups in which the alkyl moiety is a straight chain or branched chain alkyl group having 1 to 5 carbon atoms, such hydroxyalkyl groups including, for example, hydroxymethyl, 2-hydroxyethyl, 3-hydroxypropyl, 2-hydroxypropyl, 4-hydroxybutyl, 3-hydroxybutyl, 2-methyl-3-hydroxypropyl, 5-hydroxypentyl, 4-hydroxypentyl, 2-methyl-4-hydroxybutyl, 2-methyl-5-hydroxypentyl, 2-methyl-4-hydroxypentyl, etc.

Examples of the cycloalkyl group are cycloalkyl groups having 3 to 8 carbon atoms such as cyclopropyl, cyclobutyl, cyclopentyl, cyclohexyl, cycloheptyl, cyclooctyl, etc.

Examples of the aminoalkyl group are aminoalkyl groups in which the alkyl moiety is a straight chain or branched chain alkyl group having 1 to 5 carbon atoms such as aminomethyl, aminoethyl, 2-aminoethyl, aminopropyl, aminobutyl, aminopentyl and the like.

Examples of the dialkylaminoalkyl group are dialkylaminoalkyl groups wherein the aminoalkyl moiety is a straight chain or branched chain aminoalkyl group having 1 to 6 carbon atoms and substituted on the nitrogen atom with 2 straight chain or branched chain alkyl groups having about 1 to about 4 carbon atoms such as dimethylaminomethyl, diethyl-aminomethyl, 2-dimethylaminoethyl, 2-diethylaminoethyl, dimethylaminopropyl, diethylaminopropyl, dimethylaminobutyl, diethylaminobutyl, dimethylaminopentyl, diethylaminopentyl and the like.

Examples of the pyridyl group represented by R$^5$ and optionally substituted with a lower alkyl group are 2-pyridyl, 3-pyridyl, 4-pyridyl, 1-methyl-4-pyridyl, etc.

The polymer (2) of the invention can be prepared by polymerizing at least one of glycoside derivatives (1), or a combination of the derivative (1) and a compound copolymerizable therewith. This process eliminates the need for protecting the hydroxyl groups of the sugar and thus can produce with extreme ease a polymer wherein the saccharide residues having no protective group are attached as side chains. The process can produce a polymer having the contemplated properties because the sugar content of the polymer can be regulated as desired. Since an acid or alkali need not be used in the process, the resulting polymer can be easily purified and can be used as it is for applications as a medical material or the like.

Usable as compounds copolymerizable with the glycoside derivative (1) are olefin-type compounds represented by the formula

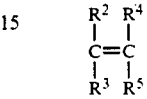 (5)

wherein R$^2$, R$^3$, R$^4$ and R$^5$ are as defined above. Examples of such compounds are as follows.

(i) Hydrophobic olefin-type compounds including alkyl esters of acrylic or methacrylic acids such as methyl methacrylate, methyl acrylate, ethyl methacrylate, ethyl acrylate, butyl methacrylate, butyl acrylate, amyl methacrylate, amyl acrylate, hexyl methacrylate, hexyl acrylate, octyl methacrylate, octyl acrylate, decyl methacrylate, decyl acrylate, undecyl methacrylate, undecyl acrylate, lauryl methacrylate, lauryl acrylate, stearyl methacrylate, stearyl acrylate, cycloalkyl esters of acrylic or methacrylic acids such as cyclopentyl acrylate or methacrylate, cyclohexyl acrylate or methacrylate, other vinyl compounds such as styrene, vinyl acetate, vinyl propionate, nitriles such as acrylonitrile, etc.

(ii) Hydrophilic olefin-type compounds such as 2-hydroxyethyl methacrylate, 2-hydroxyethyl acrylate, 2-hydroxypropyl acrylate, 2-dimethylaminoethyl acrylate or methacrylate, 2-diethylaminoethyl, acrylate or methacrylate, 3-dimethylaminopropyl acrylate or methacrylate, 3-diethylaminopropyl acrylate or methacrylate, polyethylene glycol monoacrylate or monomethacrylate, acrylamide, methacrylamide, dimethylacrylamide, dimethylmethacrylamide, acrylic acid, methacrylic acid, N-vinylpyrrolidone, vinyl carbazole and the like.

(iii) Polyfunctional olefin-type compounds such as ethylene glycol diacrylate or dimethacrylate, diethylene glycol diacrylate or dimethacrylate, triethylene glycol diacrylate or dimethacrylate, vinyl acrylate or methacrylate, allyl acrylate or methacrylate, divinylbenzene, diallylphthalate, trimethylolpropane triacrylate or trimethacrylate and the like.

The polymerization reaction can be conducted by conventional methods such as mass polymerization, solution (or homogeneous) polymerization, suspension polymerization, emulsion polymerization, radiation polymerization (using γ ray, electron beam or the like) or the like.

For example, solution polymerization is performed in a solvent in the presence or the absence of a polymerization initiator. Useful initiators are not specifically limited insofar as they are soluble in a solvent. Examples of such initiators are organic solvent-soluble initiators such as benzoyl peroxide, azobisisobutyronitrile (AIBN), di-tertiary butyl peroxide and the like, water-soluble initiators such as ammonium persulfate (APS), potassium persulfate and the like, redox-type initiators which are combinations of such initiator and $Fe^{2+}$ salt, sodium hydrogensulfite or like reducing agent, etc. Solvents for use in polymerization of at least one glycoside derivative (1) are not specifically limited insofar as they can dissolve the polymers. Examples of such solvents are water, dimethylsulfoxide (DMSO), dimethylformamide (DMF), formamide, a solvent mixture of a least two of them, etc. In copolymerization of the glycoside derivative (1) and a compound copolymerizable therewith, the solvent to be used is suitably selected according to the solubility of the resulting copolymer from, e.g. DMSO, water-containing polar solvents (methanol, isopropanol, acetone, ethyl cellosolve, etc., the water content being determined according to the solubility of the copolymer), etc. A solvent having a low chain transfer constant, such as DMSO or the like, is preferably used in preparation of a high-molecular weight polymer, whereas a solvent having a high chain transfer constant, such as isopropanol or the like, is desirable in preparation of a low-molecular weight polymer.

There is no specific restriction on the mixing ratio of the monomer component, polymerization initiator and solvent to be used in the invention. Preferable to use are less than about 5 parts by weight of the polymerization initiator and an excess amount, preferably about 200 to about 2000 parts by weight, of the solvent, per 100 parts of the monomer component.

In copolymerization of at least two different glycoside derivatives (1), the mixing ratio thereof is not specifically limited. In copolymerization of the glycoside derivative (1) and a compound copolymerizable therewith, the mixing ratio thereof is not specifically restricted and can be suitably selected according to the use of the resulting copolymer. In this case it is preferred to use about 1 to about 99% by weight, preferably about 5 to about 95% by weight, of the former.

The polymerization reaction is preferably conducted in the absence of oxygen. Oxygen can be removed from the reaction system as by usual atmosphere-replacing means such as degassing, nitrogen replacement or the like. The reaction is carried out at about 10° to about 200° C., preferably about 30° to about 120° C. and is completed in about 0.5 to about 48 hours, preferably about 2 to about 20 hours.

Suspension polymerization and emulsion polymerization can be conducted in the same manner as solution polymerization.

Mass polymerization method is suited for preparation of a copolymer from the glycoside derivative (1) and an olefin-type compound (5) since the glycoside derivative (1) is soluble in most of the foregoing olefin-type compounds (5). The mass polymerization reaction is effected in the presence or the absence of a polymerization initiator. The initiators as exemplified hereinbefore can be used. The reaction conditions are the same as those for solution polymerization.

After completion of polymerization, the polymer of the invention can be separated or collected from the reaction product and purified by usual methods, for example collected by admixing the reaction product with a poor solvent to precipitate the polymer. In preparation of a homopolymer of the glycoside derivative (1) or a copolymer of at least two different glycoside derivatives (1), methanol, ethanol, acetone or the like can be used as a poor solvent. In preparation of a copolymer of the glycoside derivative (1) and a compound copolymerizable therewith, a solvent is suitably selected since the solubility varies with the composition of components to be polymerized. The collected polymer may be further purified by, for example, reprecipitation or the like.

The thus obtained polymer of the invention has a molecular weight ranging from hundreds to thousands. The intrinsic viscosity $[\eta]$ (in DMSO, 25° C.) of the polymer is variable over a wide range of about 0.03 to about 100 depending on the polymerization degree, the kind of components used for polymerization and the like, for example about 0.03 to about 40, preferably about 0.1 to about 10 in case of the polymerization degree of about 50 to about 10000 or one to three components used.

The copolymer of the glycoside derivative (1) and a compound copolymerizable therewith has about 1 to about 99 mole %, preferably about 1 to about 95 mole %, more preferably about 5 to about 90 mole %, of repeated units (I).

The polymer of the invention is excellent in the film forming property and thus can be molded into a film, a sheet or the like by flow of the reaction product as it is on completion of the reaction.

Among the polymers of the invention, a water-soluble or water-swelling one can be rendered insoluble in water by crosslinking the hydroxyl groups of the sugar residues.

The hydroxyl groups can be crosslinked, for example, with an acid catalyst. Stated more specifically, the polymer of the invention is dissolved in a suitable solvent, an acid catalyst is added to the solution and the mixture is heated. Useful acid catalysts are not specifically limited and include p-toluenesulfonic acid, hydrochloric acid, sulfuric acid, ammonium chloride and the like. The amount of the acid catalyst used is about 0.01 to about 5 parts by weight, preferably about 0.05 to about 2 parts by weight, per 100 parts of the polymer of the invention. The solvent is suitably selected from the solvents exemplified above for polymerization. The crosslinking reaction is conducted at a temperature of about 70° to about 180° C., preferably about 80 to about 150° C. and is completed in about 1 to about 90 minutes, preferably about 5 to about 60 minutes. After completion of the reaction, the catalyst can be easily removed from the reaction system by usual methods, as by immersion of the reaction mixture in water, methanol, ethanol or the like for minutes to hours.

The hydroxyl groups can be also crosslinked with a crosslinking agent in the presence of a catalyst. Stated more specifically a catalyst and a crosslinking agent are added to a solution of the polymer of the invention and the mixture is heated. Examples of useful crosslinking agents are formalin, melamine-formaldehyde adduct, urea-formaldehyde adduct and like formalin-type crosslinking agents, methylol-type crosslinking agents, epichlorohydrin, glycidol, polyfunctional epoxy compounds (sorbitol polyglycidyl ether and the like) and like epoxy-type crosslinking agent or a methylol-type crosslinking agent, the same acid as above can be used as a catalyst. In using an epoxy-type crosslinking agent, common curing catalysts for epoxy resins can be used which include, for example, boron trifluoride, tin tetrachloride, lithium hydroxide, tri-n-butylamine, triethylamine, etc. Whichever crosslinking agent may be used, the amount of the catalyst used, type of solvent, reaction temperature, and reaction time are the same as in the foregoing crosslinking reaction using an acid catalyst alone.

Another object of the invention is to provide use of the polymer (2) of the invention.

According to the invention, there is provided a material compatible with blood and containing the polymer (2) of the invention. The materials of the invention are significantly suitable for use with organisms, highly compatible with blood, and effective in preventing thrombosis.

The materials of the invention are usable for substantially all medical instruments and materials to be contacted with blood or blood components, which include blood bypass tubes, column tubes for separation of blood cells, blood bags, artificial organs, catheters, carriers for gradual release of medicaments, etc.

The materials of the invention have a high moldability and can be molded into medical instruments or materials in the desired shape. The molding methods for the materials of the invention are not specifically limited. The materials of the invention can be molded in the same manner as in common molding of plastics.

The materials of the invention can be applied to the surface of existing molded articles of nylon, polyvinyl chloride, polystyrene glass or the like to form a coating film thereon. For application, the material of the invention is dissolved in a suitable solvent and the solution is applied to an existing molded article by brushing, immersion or like common coating methods and dried. Solvents useful for dissolving the materials of the invention can be suitably selected from the solvents exemplified above for polymerization. The solution of the material of the invention is applied in an amount not specifically limited but usually in the range sufficient to form a coating film of about 0.1 to about 100 μm, preferably about 0.5 to about 50 μm in dry thickness. The coating thus applied is dried at a temperature of about 50° to about 150° C., and may be subsequently vacuum dried when so required.

According to the invention, there is also provided a non-fogging drip-proof composition containing the polymer (2) of the invention.

The composition of the invention has a high levels of non-fogging property, drip-proofness, abrasion resistance and weatherability and the coating film of the compositions sustain these properties for a long term.

The composition of the invention can achieve such remarkable results for reasons remaining unclear. presumably the reasons may be as follows. The glycoside derivative-containing polymer (2) contains sugar residues having no protective group, namely sugar residues having hydroxyl groups all remaining free and attached to the main chain with the glycosidic linkage. The polymer of the invention contains a number of hydroxyl groups in the molecule and is marked in hydrophilic property, hence effective in preventing fogging and dripping. Since the glycoside derivative in the polymer of the invention has relatively bulky molecules, and the hydroxyl groups in the glycoside portion of the glycodise derivative partly crosslink on heating in forming a coating film, the film is given improved abrasion resistance and weatherablility. Moreover, the polymer is prevented from oozing out from the coating film due to the bulkiness of saccharide residues and crosslinking of hydroxyl groups, so that the properties of the film are sustained for a prolonged period.

The composition of the invention may contain a crosslinking agent as well as the glycoside derivative-containing polymer (2) as the effective component. The added crosslinking agent causes the hydroxyl groups in the polymer (2) to partly crosslink therewith and in case of copolymer, allows some of hydroxyl groups and/or the functional group of the compound copolymerizable with the glycoside derivative to crosslink therewith, whereby the physical properties of the film such as surface hardness are improved while the hydrophilic property of the film is substantially not reduced because most of the remaining hydroxyl groups retain the hydrophilic property of the film.

There is no specific restriction on useful crosslinking agents insofar as they can crosslink the hydroxyl groups or functional groups of the compound copolymerizable with the glycoside derivative (1). Examples of useful crosslinking agents are organic polyfunctional isocyanate compounds, polyfunctional epoxy compounds, formalin, glycidol, melamine, silicone oligomer, etc. The amount of the crosslinking agent used is suitably selected over a wide range according to the amount of the glycoside derivation in the glycoside derivative-containing polymer. For example, in case of a homopolymer, the amount of the crosslinking agent used is about 3 to about 400 parts by weight, preferably about 30 to about 200 parts by weight, per 100 parts by weight of the homopolymer. In case of a copolymer, the amount of the agent used is about 3 to about 350 parts by weight, preferably about 5 to about 150 parts by weight, per 100 parts by weight of the copolymer.

The composition of the invention may further contains a curing catalyst, colloidal silica, silane coupling agent and the like to improve the abrasion resistance, weatherablility and other properties of the film. Examples of useful curing catalysts are p-toluenesulfonic acid, triethylamine, diazabicycloundecene, hydroxide of alkali metal, phosphine, dibutyltin dilaurate, etc. Examples of useful colloidal silicas are ultrafine silica particles, ultrafine silica sols dispersed like a colloid in a hydrophilic solvent, etc. Examples of useful silane-type coupling agents are γglycidoxypropyltrimethoxysilane, γ-methacryloyloxypropyltrimethoxysilane, etc. A surfactant or the like may be added to the composition to improve the hydrophilic property of the film. The surfactant is not specifically limited and can be anionic, cationic or nonionic.

The composition of the invention can be prepared by dissolving or dispersing the polymer (2) of the invention and other components when so required in a suitable solvent. Examples of useful solvents are aromatic hydrocarbons such as toluene, xylene and the like, saturated hydrocarbons such as cyclohexane, n-hexane, octane and the like, alcohols such as methanol, ethanol, iso-propanol, butanol, iso-butanol, ethylene glycol monomethyl ether and the like, esters such as methyl acetate, ethyl acetate and the like, amides such as DMF and the like, ketones such as acetone, methyl ethyl ketone, methyl isobutyl ketone, cyclohexanone and the like, water, etc. These solvents are usable singly or at least two of them can be used in mixture. The concentration of the glycoside derivative-containing polymer in the composition of the invention is suitably selected over a wide range without specific limitation but usually in the range of about 2 to about 80% by weight, preferably about 5 to about 50% by weight, based on the whole composition.

A substrate of transparent material such as glass, plastics or the like can be improved in the non-fogging property and drip-proofness by applying the composition of the invention to the substrate to form a coating film. Stated more specifically, the composition of the invention is applied to the surface of such substrate and cured to form a coating film having non-fogging property and drip-proofness. The amount of the composition of the invention to be applied is not specifically limited, but is in a range sufficient to provide a cured film about 1 to about 500 μm, preferably about 3 to about 100 μm in thickness. The composition is cured usually at room temperature, or when required, may be cured by heating to a temperature of from higher than room temperature to about 2000° C., preferably about 50° to about 200° C. To improve the adhesion between the substrate and the film, the substrate surface may be subjected to an activating gas treatment, sandblasted or chemically treated with an acid, base, oxidizing agent or the like, or a primer coating may be formed on the substrate.

The composition of the invention may be mixed with a transparent material prior to molding.

The composition of the invention can be used for substantially all of plastics, glass and articles of such materials, for example, goggles, plastics lenses, plastics containers and like plastics articles, glass bodies, glass lenses for spectacles and like glass articles.

EXAMPLES

The present invention will be described below in greater detail with reference to the following Examples.

Given below are Examples 1 to 34 illustrating the preparation of glycoside derivatives (monomeric compounds).

EXAMPLE 1

A 19.4 g quantity of methyl glucoside (STA-MEG 106, product of Horizon Chemical A. E. Staley Manufacturing Co.) was suspended in 140 ml of 2-hydroxyethyl methacrylate. To the suspension were added 2.6 g of hydroquinone monomethyl ether and 1.0 g of phosphomolybidic acid, and the mixture was stirred well and gradually heated. After heating to a temperature of 80° to 90° C., the mixture was further stirred for about 2 hours while maintaining the same temperature and was neutralized with 2N sodium hydroxide. The obtained reaction mixture was concentrated under reduced pressure and subjected to silica gel chromatography (eluent, chloroform:methanol=9:1). A fraction ($R_f$=0.2) of the reaction mixture was concentrated, giving 20.1 g of galactosyloxyethyl acrylate (HEMA-Glc) as an oily product (yield 68.8%).

The analysis of the obtained compound gave the following results.

Silica gel TLC: 1 spot
Silica gel plate; product of Merck & Co., Inc., 60F254
Eluent; chloroform:methanol=4:1
Infrared absorption spectrum analysis (liquid film method, $cm^{-1}$):

FIG. 1 shows the IR spectrum of the above compound. Major peaks were as follows. 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of groups such as $CH_2$, $CH_3$ and the like) 1050 (broad absorption indicated by a peak in a shape peculiar to sugar residue)

Figure 2:
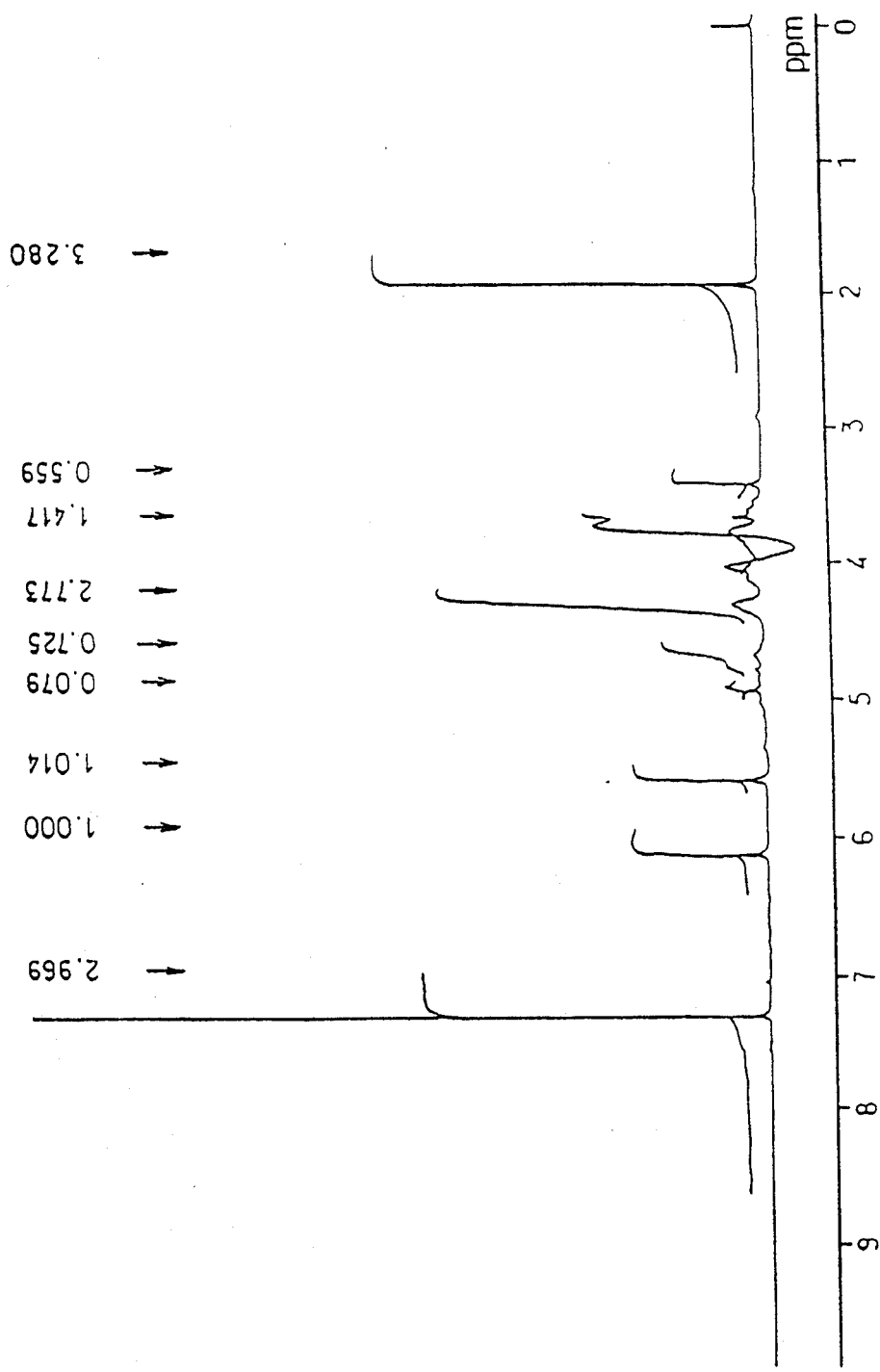
FIG. 2 shows the $^1$H-NMR spectrum of galactosyloxyethyl acrylate.

$^1$H-NMR: δ ppm (in $D_2O$):

FIG. 2 shows the $^1$H-NMR spectrum of the above compound. Major peaks were as follows. 6.1, 5.6 ($CH_2$=) 4.9 (α-anomer hydrogen) 4.2-4.6 (—$OCH_2$—) 3.2-4.2 (sugar skeleton) 1.9 ($CH_3$).

| | Elementary analysis | | |
|---|---|---|---|
| | C | H | O |
| Found | 49.2% | 7.0% | 43.8% |
| Calcd. | 49.3% | 6.9% | 4.38% |

EXAMPLE 2

A 20.0 g quantity of methyl β-D-galactoside (product of Nacalai Co., Ltd., a guaranteed reagent)was suspended in 150 ml of 2-hydroxyethyl acrylate. To the suspension were added 1.0 g of butylhydroxytoluene and 1.0 g of phosphomolybdic acid, and the mixture was stirred well and gradually heated. After heating to a temperature of 60° to 70° C., the mixture was further stirred for about 2 hours while maintaining the same temperature, and was neutralized with 2N sodium hydroxide. The obtained reaction mixture was purified in the same manner as in Example 1. A fraction ($R_f$=0.2) of the reaction mixture was concentrated, giving 15.8 g of galactosyloxyethylacrylate (HEA-Gal) as an oily product (yield 55%).

The analysis of the obtained compound gave the following results.

Silica gel TLC: 1 spot
Silica gel plate; product of Merck & Co., Inc., 60F254
Eluent; chloroform:methanol=4:1
Infrared absorption spectrum analysis (liquid film method, $cm^{-1}$): 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of $CH_2$ and the like) 1050 (broad absorption indicated by a peak in a shape peculiar to sugar residue)

$^1$H-NMR: δ ppm (in $D_2O$): 5.6-6.8 ($CH_2$=CH—) 4.9 (α-anomer hydrogen) 4.2-4.5 (—$OCH_2$—) 3.4-4.2 (sugar skeleton).

| | Elementary analysis | | |
|---|---|---|---|
| | C | H | O |
| Found | 47.3% | 6.6% | 46.1% |
| Calcd. | 47.5% | 6.5% | 46.0% |

EXAMPLE 3 TO 11

The desired compounds were prepared by the same procedure as in Example 1 with the exception of using the following starting compounds and catalysts.

EXAMPLE 3

Starting compounds:

| Methyl β-D-galactoside | 19.4 g |
|---|---|
| 2-Hydroxyethyl methacrylate | 140 ml |
| Catalyst: Silicotungstic acid | 1.0 g |

Figure 3:
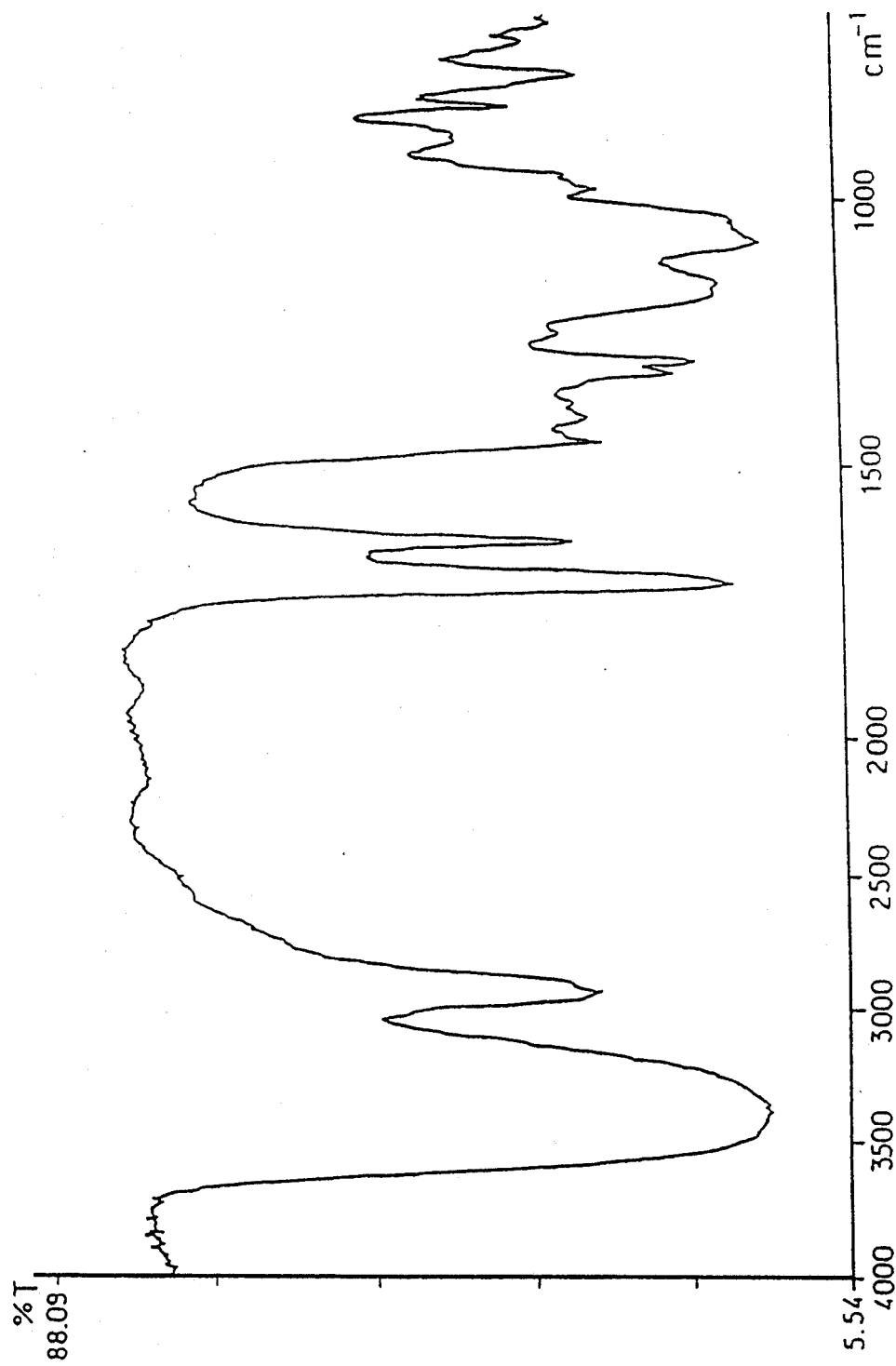
FIG. 3 shows the IR spectrum of galactosylethyl methacrylate.

Desired compound:
Galactosyloxyethyl methacrylate (HEMA-Gal)
Yield: 22.0 g (72%)
Infrared absorption spectrum analysis (liquid film method, $cm^{-1}$):
FIG. 3 shows the IR spectrum of the obtained compound. Major peaks were as follows. 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of groups such as $CH_2$, $CH_3$ and the like) 1050 (broad absorption indicated by a peak in a shape peculiar to sugar residue)

Figure 4:
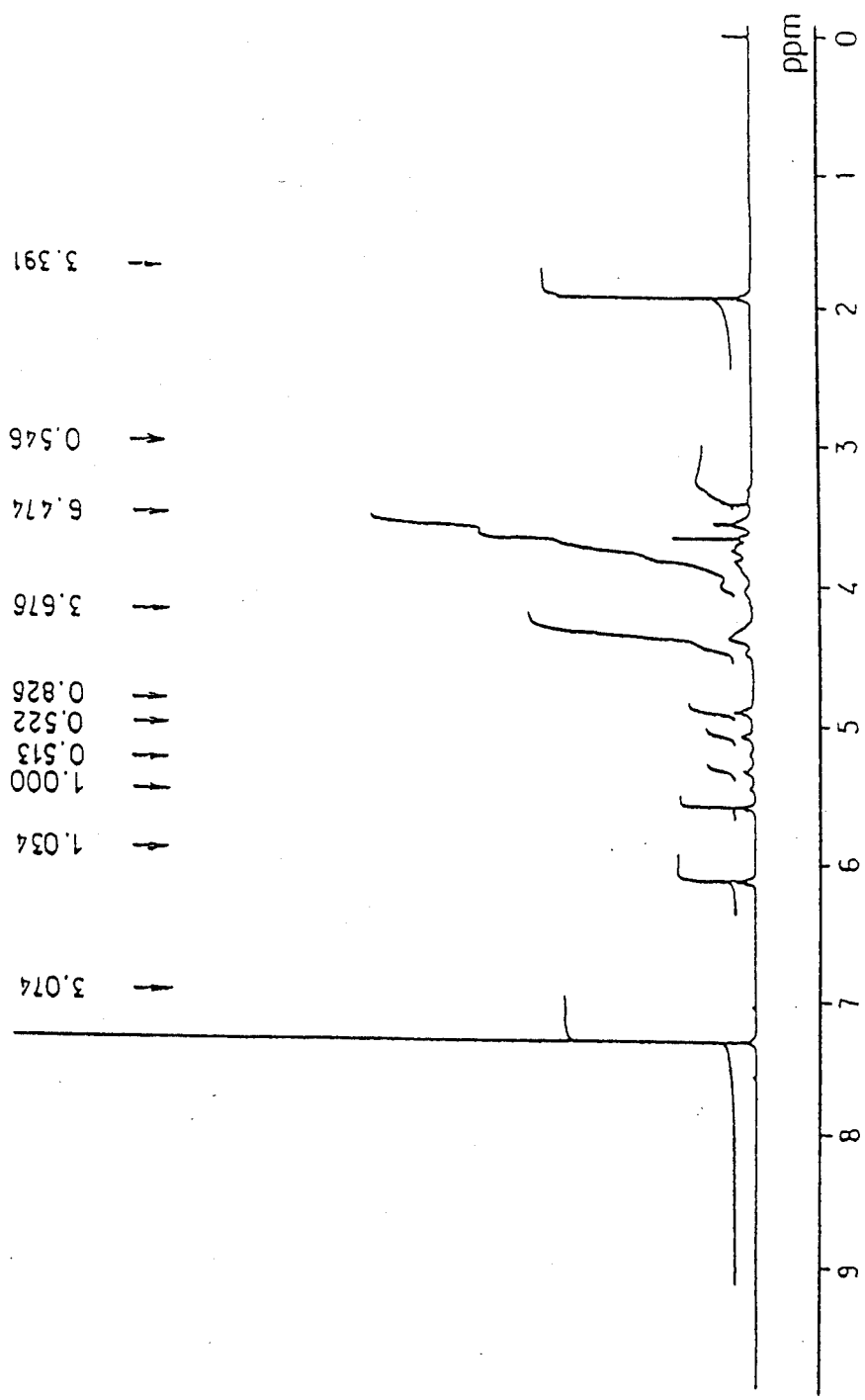
FIG. 4 shows the $^1$H-NMR spectrum of galactosyloxyethyl methacrylate.

$^1$H-NMR: δ ppm (in $D_2O$):

FIG. 4 shows the $^1$H-NMR spectrum of the above compound. Major peaks were as follows. 6.1, 5.6: $CH_2$=; 4.9: α-anomer hydrogen; 4.2-4.5: —$OCH_2$—; 3.2-4.2: sugar skeleton; 1.9: $CH_3$.

| | Elementary analysis | | |
|---|---|---|---|
| | C | H | O |
| Found | 49.0% | 6.9% | 44.1% |
| Calcd. | 49.3% | 6.9% | 43.8% |

EXAMPLE 4

Starting compounds:

| Methyl β-D-mannoside | 19.4 g |
|---|---|
| 2-Hydroxyethyl methacrylate | 140 ml |
| Catalyst: Phosphomolybdic acid | 1.0 g |

Desired compound:
Mannosyloxyethyl methacrylate (HEMA-Man)
Yield: 18.5 g (63%)
Infrared absorption spectrum analysis (liquid film method, cm$^{-1}$):
Silica gel plate; product of Merck & Co., Inc., 60F254
Eluent: chloroform:methanol = 4:1
Infrared absorption spectrum analysis (liquid film method, cm$^{-1}$): 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of groups such as $CH_2$, $CH_3$ and the like) 1050 (broad absorption indicated by a peak in a shape peculiar to sugar residue)

$^1$H-NMR: δ ppm (in $D_2O$): 6.1, 5.6: $CH_2$=; 4.9: α-anomer hydrogen; 4.2-4.5: —$OCH_2$13; 3.2-4.2: sugar skeleton; 1.9: $CH_3$.

| | Elementary analysis | | |
|---|---|---|---|
| | C | H | O |
| Found | 49.1% | 7.0% | 43.9% |
| Calcd. | 49.3% | 6.9% | 43.8% |

EXAMPLE 5

Starting compounds:

| β-D-xyloside | 16.4 g |
|---|---|
| 2-Hydroxyethyl methacrylate | 140 ml |
| Catalyst: Silicotungstic acid | 1.0 g |

Desired compound:
Xylosyloxyethyl methacrylate (HEMA-Xyl)
Yield: 18.0 g (69%
Infrared absorption spectrum analysis (liquid film method, cm$^{-1}$): 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of groups such as $CH_2$, $CH_3$ and the like) 1050 (broad absorption indicated by a peak in a shape peculiar to sugar residue)

$^1$H-NMR: δ ppm (in $D_2O$): 6.1, 5.6: $CH_2$=; 4.9: α-anomer hydrogen; 4.2-4.5: sugar skeleton; 1.9: $CH_3$.

| | Elementary analysis | | |
|---|---|---|---|
| | C | H | O |
| Found | 49.8% | 6.9% | 43.3% |
| Calcd. | 50.3% | 6.9% | 42.7% |

EXAMPLE 6

Starting compounds:

| Methyl glucoside | 19.4 g |
|---|---|
| 2-Hydroxypropyl methacrylate | 150 ml |
| Catalyst: Phosphomolybdic acid | 1.0 g |

Figure 5:
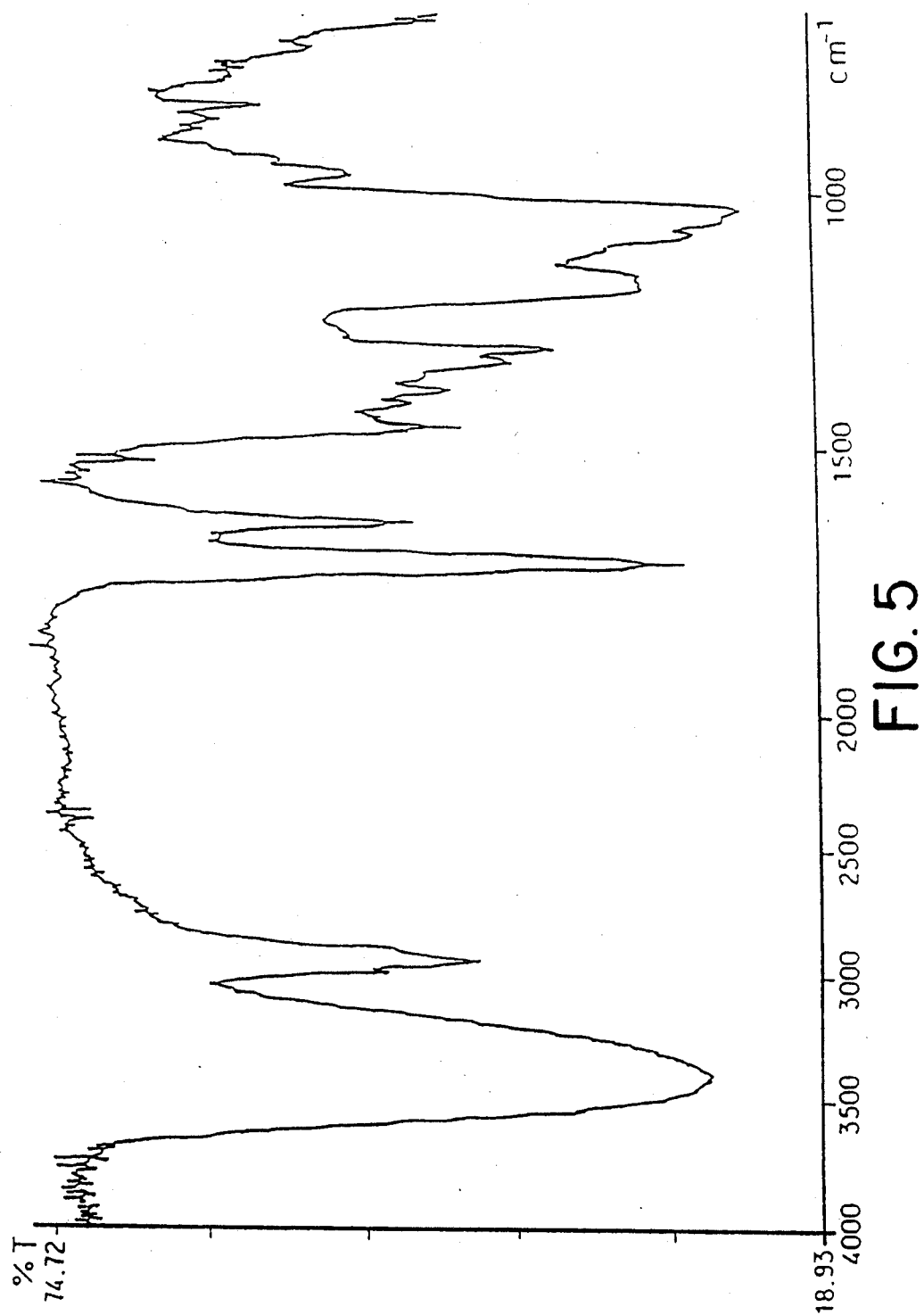
FIG. 5 shows the IR spectrum of glucosyloxypropyl methacrylate.

Desired compound:
Glucosyloxypropyl methacrylate (HPMA-Glc)
Yield: 15.6 g (43%)
Infrared absorption spectrum analysis (liquid film method, cm$^{-1}$):
FIG. 5 shows the IR spectrum of the above compound. Major peaks were as follows. 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of $CH_2$, $CH_3$ and the like) 1050 (broad absorption indicated by a peak in a shape peculiar to sugar residue)

$^1$H-NMR: δ ppm (in $D_2O$): 6.1, 5.6: $CH_2$=; 4.9: α-anomer hydrogen; 4.2-4.5: —$OCH_2$—; 3.2-4.2: sugar skeleton; 1.9: $CH_3$ (methacryl group); 1.3: $CH_3$ (propylene).

| | Elementary analysis | | |
|---|---|---|---|
| | C | H | O |
| Found | 49.6% | 7.3% | 43.1% |
| Calcd. | 51.0% | 7.2% | 41.8% |

Example 7

Starting compounds:

| Methyl glucoside | 19.4 g |
|---|---|
| 2-Hydroxyethyl acrylate | 120 ml |
| Catalyst: Phosphomolybdic acid | 1.0 g |

Figure 6:
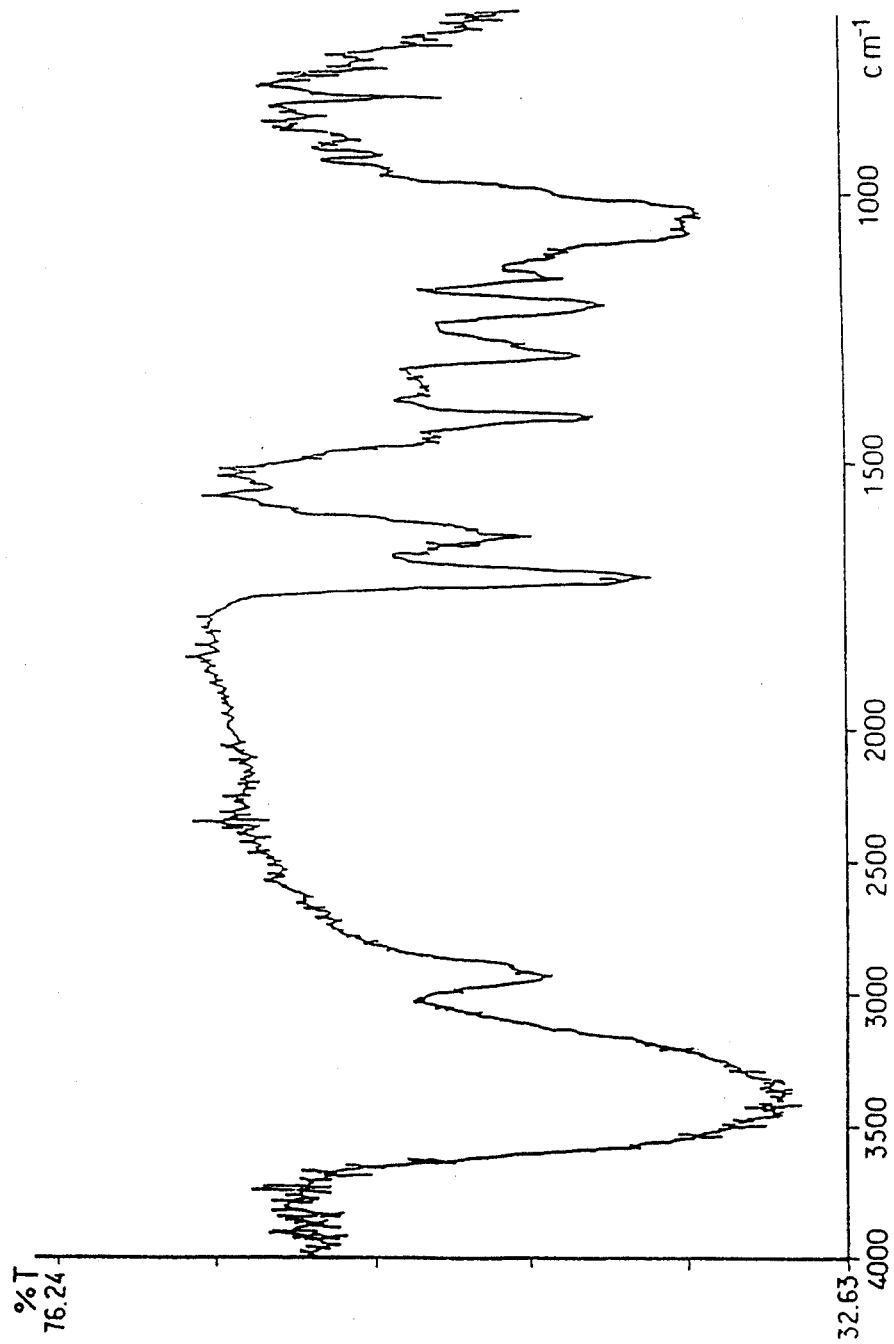
FIG. 6 shows the IR spectrum of glucosyloxyethyl acrylate.

Desired compound:
Glucosyloxy ethyl acrylate (HEA-Glc)
Yield: 22.5 g (81%)
Infrared absorption spectrum analysis (liquid film method, cm$^{-1}$):
FIG. 6 shows the IR spectrum of the foregoing compound. Major peaks were as follows. 3400 (broad absorption due to O—H stretching) 2940 (absorption due to C—H stretching) 1710 (absorption due to C=O, carbonyl group) 1630 (absorption due to C=C, double bond) 1450 (absorption due to deformation vibrations of CH$_2$ and the like) 1050 absorption indicated by a peak in a shape peculiar to sugar residue)

$^1$H-NMR: δ ppm (in D$_2$O): 5.6-6.8: CH$_2$=CH—; 4.9: α-anomer hydrogen ; 4.2-4.5: —OCH$_2$—; 3.2-4.2: sugar skeleton.

|       | Elementary analysis | | |
|-------|------|------|------|
|       | C    | H    | O    |
| Found | 47.1% | 6.5% | 46.4% |
| Calcd. | 47.5% | 6.5% | 46.0% |

Example 8

Starting compounds:

| Methyl glucoside | 19.4 g |
|---|---|
| 2-Hydroxyethyl acrylate | 140 ml |
| Catalyst: Phosphomolybdic acid | 1.0 g |

Desired compound:

Glucosyloxy propyl acrylate (HPA-Glc)

Yield: 14.0 g (48%)

Infrared absorption spectrum analysis (liquid film method, cm$^{-1}$): 3400 (broad absorption due to O—H stretching) 2950 (absorption due to C—H stretching) 1710 (absorption due to C=O, carbonyl group) 1630 (absorption due to C=C, double bond) 1450 (absorption due to deformation vibrations of CH$_2$, CH$_3$ and the like) 1050 (broad absorption indicated by a peak in a shape peculiar to sugar residue)

$^1$H-NMR: δ ppm (in D$_2$O): 5.6-6.8: CH$_2$=CH—; 4.9: α-anomer hydrogen; 4.2-4.5: —OCH$_2$—; 3.2-4.2: sugar skeleton; 1.3: CH$_3$.

|       | Elementary analysis | | |
|-------|------|------|------|
|       | C    | H    | O    |
| Found | 48.9% | 7.0% | 44.1% |
| Calcd. | 49.3% | 6.9% | 43.8% |

Example 9

Starting compounds:

| Methyl glucoside | 19.4 g |
|---|---|
| Diethylene glycol methacrylate | 180 ml |
| Catalyst: Phosphomolybdic acid | 1.0 g |

Desired compound:

Glucosyloxy ethoxyethyl methacrylate (HEEMA-Glc)

Yield: 22.5 g (67%)

Infrared absorption spectrum analysis (liquid film method, cm$^{-1}$): 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of CH$_2$, CH$_3$ and the like) 1050 (broad absorption indicated by a peak in a shape peculiar to sugar residue)

$^1$H-NMR: δ ppm (in D$_2$O): 6.1, 5.6: CH$_2$=; 4.9: α-anomer hydrogen; 3.2-4.5: —OCH$_2$—, sugar skeleton; 1.9: CH$_3$.

|       | Elementary analysis | | |
|-------|------|------|------|
|       | C    | H    | O    |
| Found | 49.7% | 7.3% | 43.0% |
| Calcd. | 50.0% | 7.2% | 42.8% |

Example 10

Starting compounds:

| Methyl β-D-galactoside | 19.4 g |
|---|---|
| Diethylene glycol methacrylate | 180 ml |
| Catalyst: Phosphomolybdic acid | 1.0 g |

Desired compound:

Galactosyloxy ethoxyethyl methacrylate (HEEMA-Gal)

Yield: 24.2 (72%)

Infrared absorption spectrum analysis (liquid film method, cm$^{-1}$): 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of CH$_2$, CH$_3$ and the like) 1050 (broad absorption indicated by a peak in a shape peculiar to sugar residue)

$^1$H-NMR: δ ppm (in D$_2$O): 6.1, 5.6: CH$_2$=; 4.9: α-anomer hydrogen; 3.2-4.5: —OCH$_2$—, sugar skeleton; 1.9: CH$_3$.

|       | Elementary analysis | | |
|-------|------|------|------|
|       | C    | H    | O    |
| Found | 49.6% | 7.3% | 43.1% |
| Calcd. | 50.0% | 7.2% | 42.8% |

Example 11

Starting compounds:

| Methyl glucoside | 19.4 g |
|---|---|
| Diethylene glycol acrylate | 160 ml |
| Catalyst: Phosphomolybdic acid | 1.0 g |

Desired compound:

Glucosyloxy ethoxyethyl acrylate (HEEA-Glc)

Yield: 21.3 g (66%)

Infrared absorption spectrum analysis (liquid film method, cm$^{-1}$): 3400 (broad absorption due to O—H stretching) 2940 (absorption due to C—H stretching) 1710 (absorption due to C=O, carbonyl group) 1630 (absorption due to C=C, double bond) 1450 (absorption due to deformation vibrations of CH$_2$ and the like) 1050 (broad absorption indicated by a peak in a shape peculiar to sugar residue)

$^1$H-NMR: δ ppm (in D$_2$O): 5.6-6.8: CH$_2$=CH—; 4.9: β-anomer hydrogen; 3.4-4.5: —OCH$_2$—, sugar skeleton; 1.9: CH$_3$.

|       | Elementary analysis | | |
|-------|------|------|------|
|       | C    | H    | O    |
| Found | 47.8% | 7.0% | 45.2% |
| Calcd. | 48.4% | 6.9% | 44.7% |

EXAMPLE 12

A 2.0 g quantity of methyl D-maltotrioside was suspended in 15 ml of diethylene glycol methacrylate. To the suspension were added 0.1 g of butylhydroxytoluene and 0.2 g of phosphomolybdic acid, and the mixture was stirred well and gradually heated. After heating to a temperature of 70° to 80° C., the mixture was further stirred for about 2.5 hours while maintaining the same temperature and was neutralized with 2N sodium hydroxide. To the reaction mixture was added 30 ml of ethyl acetate and the resulting mixture was extracted with water, followed by concentration of the aqueous layer under reduced pressure. The obtained oily product was subjected to silica gel chromatography (eluent, chloroform:methanol=4:1 to 1:1). A fraction ($R_f$=0.2) of the reaction mixture was concentrated, giving 1.28 g of maltotriosyloxyethyl methacrylate (HEEMA-Glc3) as an oily product (yield 49%).

The analysis of the obtained compound showed the following results.

Silica gel TLC: 1 spot

Silica gel plate; product of Merck % Co., Inc., 60F254

Eluent, chloroform:methanol=4:1

Infrared absorption spectrum analysis (liquid film method, cm$^{-1}$): 3400 (broad absorption due to O—H stretching) 2940 (absorption due to C—H stretching) 1710 (absorption due to C=O, carbonyl group) 1640 (absorption due to C=C, double bond) 1450 (absorption due to deformation vibrations of $CH_2$, $CH_3$ and the like) 1050 (broad absorption indicated by a peak in a shape peculiar to sugar residue)

$^1$H-NMR: δ ppm (in $D_2O$): 6.1, 5.6 ($CH_2$=) 5.2 (α-anomer hydrogen) 3.2-4.5 (—$OCH_2$—, sugar skeleton) 1.9 ($CH_3$).

|  | Elementary analysis | | |
| --- | --- | --- | --- |
|  | C | H | O |
| Found | 47.2% | 6.7% | 46.1% |
| Calcd. | 47.3% | 6.7% | 46.0% |

EXAMPLES 13 TO 14

The desired compounds were prepared in the same manner as in Example 3 with the exception of using the following starting compounds, catalysts and polymerization inhibitors.

EXAMPLE 13

Starting compounds:

| Methyl D-maltoside | 3.6 g |
| --- | --- |
| 2-Hydroxyethyl methacrylate | 20 ml |
| Catalyst: Phosphomolybdic acid | 0.1 g |
| Polymerization inhibitor: | 0.3 g |
| Hydroquinone monomethyl ether | |

Desired compound:
Maltosyloxyethyl methacrylate (HEMA-Mal)
Yield: 1.8 g (40%)
Infrared absorption spectrum analysis (liquid film method, cm$^{-1}$)
3400 (broad absorption due to O—H stretching)
2940 (absorption due to C—H stretching)
1710 (absorption due to C=O, carbonyl group)
1640 (absorption due to C=C, double bond)
1450 (absorption due to deformation vibrations of $CH_2$, $CH_3$ and the like)
1050 (broad absorption indicated by a peak in a shape peculiar to sugar residue)

$^1$H-NMR: δ ppm (in $D_2O$): 6.1, 5.6: $CH_2$=; 4.9: α-anomer hydrogen; 3.2-4.5: —$OCH_2$—, sugar skeleton; 1.9: $CH_3$.

|  | Elementary analysis | | |
| --- | --- | --- | --- |
|  | C | H | O |
| Found | 47.0% | 6.7% | 46.3% |
| Calcd. | 47.6% | 6.7% | 45.8% |

EXAMPLE 14

Starting compounds:

| Methyl β-D-lactoside | 3.6 g |
| --- | --- |
| 2-Hydroxyethyl methacrylate | 20 ml |
| Catalyst: Phosphomolybdic acid | 0.1 g |
| Polymerization inhibitor: | 0.3 g |
| Hydroquinone monomethyl ether | |

Desired compound:
Lactosyloxy ethyl methacrylate (HEMA-Lac)
Yield: 1.5 g (33%)
Infrared absorption spectrum analysis (liquid film method, cm$^{-1}$):
3400 (broad absorption due to O—H stretching)
2940 (absorption due to C—H stretching)
1710 (absorption due to C=O, carbonyl group)
1640 (absorption due to C=C, double bond)
1450 (absorption due to deformation vibrations of $CH_2$, $CH_3$ and the like)
1050 (broad absorption indicated by a peak in a shape peculiar to sugar residue)

$^1$H-NMR: δ ppm (in $D_2O$): 6.1, 5.6: $CH_2$=; 4.9: α-anomer hydrogen; 3.2-4.5: —$OCH_2$—, sugar skeleton; 1.9: $CH_3$.

|  | Elementary analysis | | |
| --- | --- | --- | --- |
|  | C | H | O |
| Found | 47.0% | 6.8% | 46.2% |
| Calcd. | 47.6% | 6.7% | 45.8% |

EXAMPLE 15

Ninety grams of dextrose was suspended in 650 ml of 2-hydroxyetyl methacrylate. To the suspension were added 1.0 g of hydroquinone monomethyl ether and 0.5 g of p-toluenesulfonic acid, and the mixture was heated while blowing the air into the mixture. After heating to about 110° C., the mixture was stirred for 2 hours while maintaining the same temperature and was cooled, followed by neutralization with sodium bicarbonate. The obtained reaction mixture was concentrated under reduced pressure and purified by silica gel chromatography (eluent, chloroform: methanol=1:0 to 1:1, gradient elution), giving 110 g of HEMA-Glc as the desired product (yield 75%). The obtained compound was identical in the analysis data with the compound produced in Example 1.

EXAMPLES 16 TO 19

HEMA-Glc was obtained as the desired product by the same procedure as in Example 15 with the exception of using the catalysts in specific amounts and the polymerization inhibitors as shown in Table 1. The resulting products were identical in the analysis data with the compound obtained in Example 1.

TABLE 1

| | Catalyst | | Polymerization | Yield | |
|---|---|---|---|---|---|
| | Kind | Amount (g) | inhibitor | (g) | (%) |
| Ex. 16 | ClSO$_3$H | 0.1 | MMHQ | 112 | 77 |
| Ex. 17 | DSA | 0.5 | MMHQ | 100 | 68 |
| Ex. 18 | ABS | 0.5 | MMHQ | 93 | 64 |
| Ex. 19 | FeCl$_3$ | 1.0 | BHT | 99 | 68 |

ClSO$_3$H: chlorosulfonic acid
DSA: laurylsulfuric acid
ABS: laurylbenzenesulfonic acid
FeCl$_3$: ferric chloride
MMHQ: hydroquinone monomethyl ether
BHT: butylhydroxytoluene

EXAMPLES 20 TO 22

The same procedure as in Example 15 was repeated with the exception of using the following starting compounds and catalysts, giving the desired compounds.

EXAMPLE 20

Starting compounds:

| | |
|---|---|
| Methyl β-D-galactoside | 90 g |
| 2-Hydroxyethyl methacrylate | 650 ml |
| Catalyst: p-Toluenesulfonic acid | 0.2 g |
| Polymerization inhibitor: Butylhydroxytoluene | 1.0 g |

Desired compound: HEMA-Gal
Yield: 115 g (79%)
The obtained product was identical in the analysis data with the compound prepared in Example 3.

EXAMPLE 21

Starting compounds:

| | |
|---|---|
| Dextrose | 80 g |
| 2-Hydroxyethyl acrylate | 600 ml |
| Catalyst: p-Toluenesulfonic acid | 0.2 g |
| Polymerization inhibitor: Butylhydroxytoluene | 1.0 g |

Desired compound: HEA-Glc
Yield: 110 g (79%)
The obtained product was identical in the analysis data with the compounds prepared in Example 7.

EXAMPLE 22

Starting compounds:

| | |
|---|---|
| Dextrose | 80 g |
| Diethylene glycol methacrylate | 880 ml |
| Catalyst: Sulfuric acid | 0.2 g |

Desired compound: HEEMA-Glc
Yield: 120 g (71%)
The obtained product was identical in the analysis data with the compound produced in Example 9.

EXAMPLE 23

A 90 g quantity of dextrose was suspended in 650 ml of 2-hydroxyethyl methacrylate. Hydroquinone monomethyl ether (1.0 g) was added to the suspension and the mixture was heated while blowing the air into the mixture. After heating the mixture to about 110° C., 50 ml of 2-hydroxyethyl methacrylate having dissolved therein 0.2 g of p-toluenesulfonic acid was added while maintaining the same temperature. The obtained mixture was stirred for 2 hours and cooled. The resulting mixture was treated and purified in the same manner as in Example 15, giving 115 g of HEMA-Glc as the desired product (yield 79%). The obtained compound was identical in the analysis data with the compound prepared in Example 1.

EXAMPLE 24

The same procedure as in Example 23 was repeated with the exception of using 0.2 g of sulfuric acid in place of p-toluenesulfonic acid, giving 118 g of HEMA-Glc (yield 81%). The obtained compound was identical in the analysis data with the compound prepared in Example 1.

EXAMPLES 25 TO 32

The desired compounds were produced in the same manner as in Example 23 using the following starting compounds and catalysts.

EXAMPLE 25

Starting compounds:

| | |
|---|---|
| Galactose | 90 g |
| 2-Hydroxyethyl methacrylate | 650 ml |
| Catalyst: Sulfuric acid | 0.1 g |

Desired compound: HEMA-Gal
Yield: 113 g (77%)
The obtained product was identical in the analysis data with the compound produced in Example 3.

EXAMPLE 26

Starting compounds:

| | |
|---|---|
| Mannose | 90 g |
| 2-Hydroxyethyl methacrylate | 650 ml |
| Catalyst: p-Toluenesulfonic acid | 0.2 g |

Desired compound: HEMA-Man
Yield: 102 g (70%)
The obtained product was identical in the analysis data with the compound prepared in Example 4.

EXAMPLE 27

Starting compounds:

| | |
|---|---|
| Xylose | 75 g |
| 2-Hydroxyethyl methacrylate | 650 ml |
| Catalyst: Sulfuric acid | 0.2 g |

Desired compound: HEMA-Xyl
Yield: 97 g (74%)
The obtained product was identical in the analysis data with the compound prepared in Example 5.

EXAMPLE 28

Starting compounds:

| | |
|---|---|
| Dextrose | 80 g |
| 2-Hydroxypropyl methacrylate | 720 ml |
| Catalyst: Sulfuric acid | 0.2 g |
| Polymerization inhibitor: Butylhydroxytoluene | 1.0 g |

Desired compound: HPMA-Glc
Yield: 104 g (68%)
The obtained product was identical in the analysis data with the compound prepared in Example 6.

EXAMPLE 29

Starting compounds:

| | |
|---|---|
| Galactose | 80 g |
| 2-Hydroxyethyl acrylate | 600 ml |
| Catalyst: p-Toluenesulfonic acid | 0.2 g |

Desired compound: HEA-Gal
Yield: 114 g (82%)
The obtained product was identical in the analysis data with the compound produced in Example 2.

EXAMPLE 30

Starting compounds:

| | |
|---|---|
| Dextrose | 80 g |
| 2-Hydroxypropyl acrylate | 720 ml |
| Catalyst: p-Toluenesulfonic acid | 0.2 g |

Desired compound: HPA-Glc
Yield: 94 g (64%)
The obtained product was identical in the analysis data with the compound produced in Example 8.

EXAMPLE 31

Starting compounds:

| | |
|---|---|
| Galactose | 80 g |
| Diethylene glycol methacrylate | 880 ml |
| Catalyst: Sulfuric acid | 0.2 g |

Desired compound: HEEMA-Gal
Yield: 121 g (72%)
The obtained product was identical in the analysis data with the compound prepared in Example 10.

EXAMPLE 32

Starting compounds:

| | |
|---|---|
| Dextrose | 80 g |
| Diethylene glycol methacrylate | 180 ml |
| Catalyst: p-Toluenesulfonic acid | 0.2 g |

Desired compound: HEEA-Glc
Yield: 117 g (73%)
The obtained product was identical in the analysis data with the compound prepared in Example 11.

EXAMPLE 33

A 3.4 g quantity of maltose was suspended in 20 ml of 2-hydroxyethyl methacrylate. To the suspension was added 0.5 g of hydroquinone monomethyl ether and the mixture obtained was heated while blowing the air into the mixture. After heating the mixture to about 110° C., 1.0 ml of 2-hydroxyethyl methacrylate having dissolved therein 0.01 g of p-toluenesulfonic acid was added while maintaining the same temperature. The resulting mixture was stirred for 2 hours and cooled. The obtained reaction mixture was then treated and purified in the same manner as in Example 15, giving 1.5 g of HEMA-Mal as the desired compound (yield 33%). The obtained product was identical in the analysis data with the compound prepared in Example 13.

EXAMPLE 34

The same procedure as in Example 34 was repeated with the exception of using lactose in place of maltose, giving 1.2 g of HEMA-Lac as the desired compound (yield 26%). The obtained product was identical in the analysis data with the compound produced in Example 14.

Given below are Examples 35 to 86 illustrating the preparation of glycoside derivative-containing polymers.

EXAMPLE 35

Ten grams of glucosyloxyethyl methacrylate (HEMA-Glc) was dissolved in 70 ml of distilled water. To the solution was added 40 mg of ammonium persulfate (APS), and the mixture was reacted with stirring at 50° C. for 12 hours in a nitrogen stream. After completion of the reaction, the reaction mixture was poured into 1 l of acetone, and the precipitated while crystals were collected by filtration, washed with acetone and dried under reduced pressure. The obtained white precipitate was dissolved in 100 l of distilled water and the solution was poured into 1 l of acetone. The precipitate was collected by filtration and dried under reduced pressure, giving 9.5 g of poly (glucosyloxyethyl methacrylate) as a white powder (yield 95%).

Figure 7:
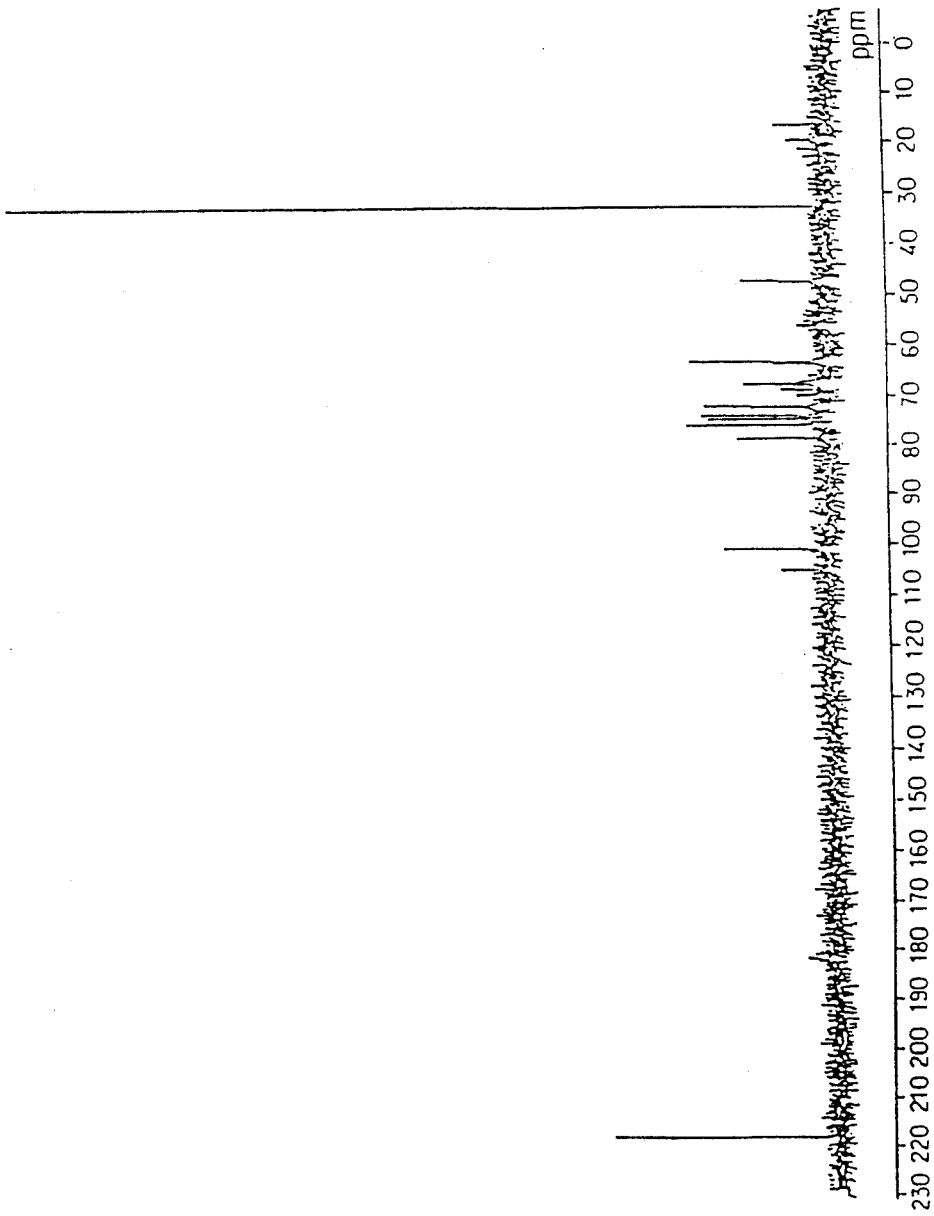
FIG. 7 shows the $^{13}$C-NMR spectrum of poly(-glucosyloxyethyl methacrylate).

Infrared absorption spectrum analysis (liquid film method, cm$^{-1}$):

3400 (broad peak due to O—H, hydroxyl group of sugar residue)
2940 (C—H)
1720 (C=O, carbonyl methacrylate)
1260 (broad peak)
1050 (broad peak peculiar to sugar residue)
$^{13}$C—NMR: δppm (DMSO-D$_6$):
FIG. 7 shows the $^{13}$C-NMR spectrum of the above compound.

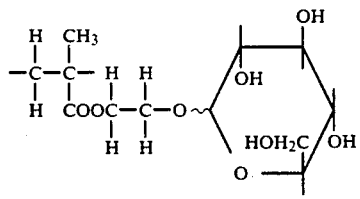

Figure 8:
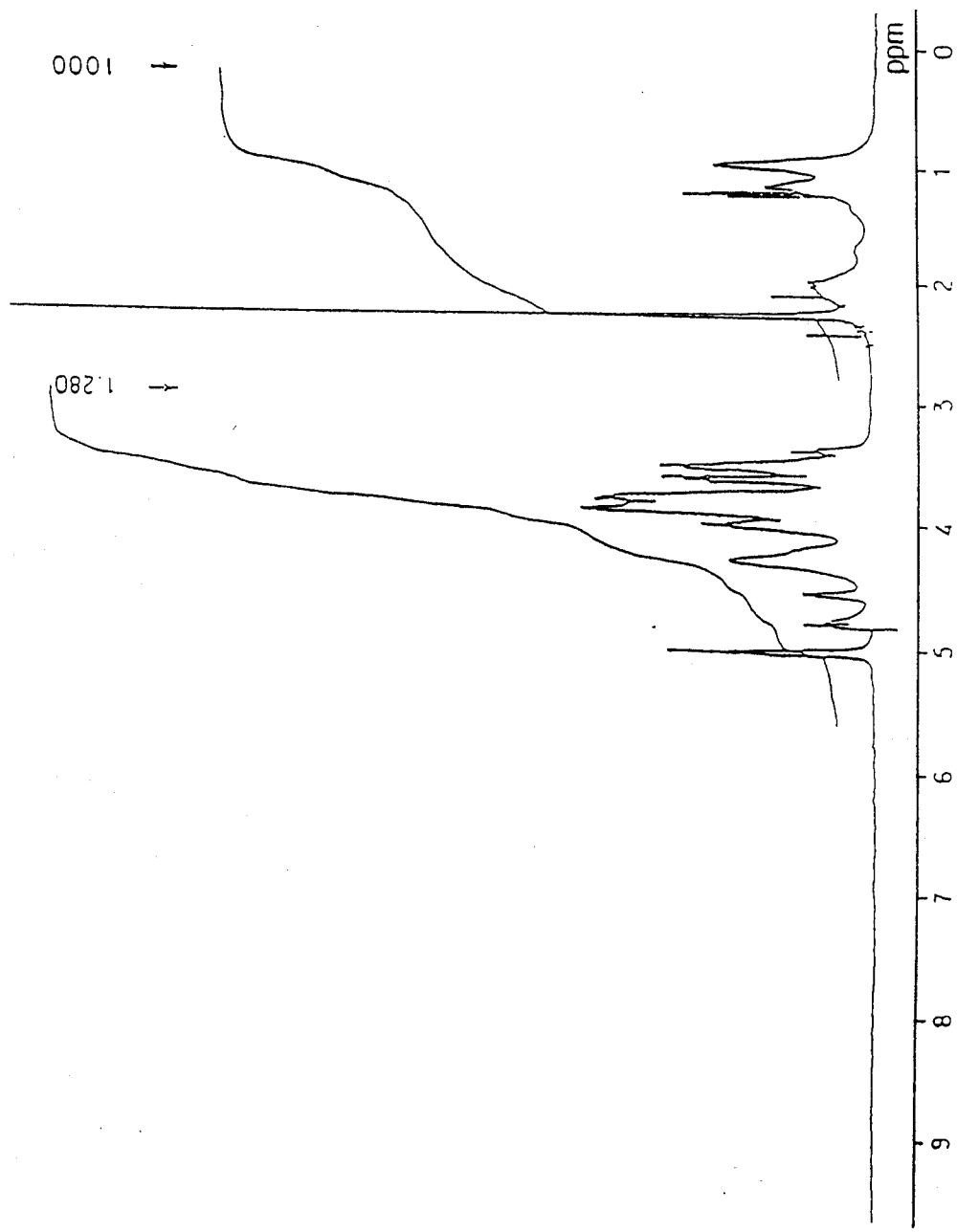
FIG. 8 shows the $^1$H-NMR spectrum of poly(-glucosyloxyethyl methacrylate).

$C_1$: 98 (α-anomer) 103 (β-anomer) $C_2$, $C_3$, $C_4$, $C_5$, $C_6$, $C_5'$ and $C_6'$: 61–76 (ten-odd sharp peaks), $C_1'$: 45, $C_2'$: 54, $C_3'$: 17, 19, $C_4'$: 178, 179, FIG. 8 shows the $^1$H-NMR spectrum of the above compound.

EXAMPLE 36

A 10 g quantity of galactosyloxyethyl methacrylate (HEMA-Gal) was dissolved in 70 ml of DMSO. To the solution was added 25 mg of AIBN, and the mixture was reacted with stirring at 65° C. for 12 hours in a nitrogen stream. After completion of the reaction, the polymer was recovered by precipitation with acetone in the same manner as in Example 35, purified by reprecipitation and dried under vacuum, giving 8.9 g of poly (galactosyloxy ethyl methacrylate) as a white powder (yield 89%).

Infrared absorption spectrum analysis (liquid film method, cm$^{-1}$):

The obtained product showed a spectrum similar to that obtained in Example 35.

$^{13}$C-NMR: δ ppm (DMSO-D$_6$):

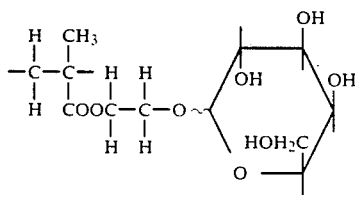

C$_1$: 98 (α-anomer) 103 (β-anomer) C$_2$, C$_3$, C$_4$, C$_5$, C$_6$, C$_5$' and C$_6$': 61–76 (ten-odd sharp peaks) C$_1$': 45, C$_2$': 54, C$_3$': 17, 19, C$_4$': 178, 179

EXAMPLES 37 TO 48

Homopolymers were obtained in the same manner as in Example 35 with the exception of using the monomers, solvents for polymerization (distilled water) in specified amounts (g), polymerization initiator (ammonium persulfate) in specified amounts (mg) and the reaction time (hour), as shown below in Table 2.

TABLE 2

| | Monomer | Amount of water | Amount of initiator | Time | Yield (g) | (%) |
|---|---|---|---|---|---|---|
| Ex. 37 | HEA-Gal | 70 | 40 | 12 | 9.6 | 96 |
| Ex. 38 | HEEMA-Glc3 | 60 | 30 | 12 | 9.5 | 95 |
| Ex. 39 | HEMA-Man | 70 | 40 | 10 | 9.7 | 97 |
| Ex. 40 | HEMA-Xyl | 90 | 40 | 10 | 9.4 | 94 |
| Ex. 41 | HEMA-Mal | 70 | 35 | 10 | 9.2 | 92 |
| Ex 42 | HEMA-Lac | 70 | 35 | 10 | 9.2 | 92 |
| Ex. 43 | HPMA-Glc | 70 | 40 | 10 | 9.8 | 98 |
| Ex. 44 | HEA-Glc | 70 | 40 | 10 | 9.7 | 97 |
| Ex. 45 | HPA-Glc | 70 | 40 | 10 | 9.7 | 97 |
| Ex. 46 | HEEMA-Glc | 70 | 35 | 10 | 9.0 | 90 |
| Ex. 47 | HEEMA-Gal | 70 | 35 | 10 | 8.9 | 89 |
| Ex. 48 | HEEA-Glc | 70 | 40 | 10 | 9.1 | 91 |

Table 3 below shows the intrinsic viscosity (in DMSO, 25° C.) of the homopolymers obtained in Examples 35 to 48 and the results of elementary analysis thereof.

TABLE 3

| Example No. | Intrinsic viscosity | Elementary analysis (Calcd.) | | |
|---|---|---|---|---|
| | | C | H | O |
| 35 | 1.56 | 49.0 | 7.5 | 43.5 |
| | | (49.3) | (6.9) | (43.8) |
| 36 | 1.82 | 46.7 | 8.3 | 45.0 |
| | | (49.3) | (6.9) | (43.8) |
| 37 | 1.50 | 46.2 | 6.5 | 47.3 |
| | | (47.5) | (6.5) | (46.0) |
| 38 | 2.50 | 46.0 | 6.8 | 47.2 |
| | | (47.3) | (6.7) | (46.0) |
| 39 | 1.80 | 48.5 | 7.1 | 44.4 |
| | | (49.3) | (6.9) | (43.8) |
| 40 | 1.75 | 49.1 | 7.1 | 43.8 |
| | | (50.3) | (6.9) | (42.7) |
| 41 | 2.33 | 46.3 | 6.8 | 46.9 |
| | | (47.6) | (6.7) | (45.8) |
| 42 | 2.12 | 47.3 | 6.9 | 45.8 |
| | | (47.6) | (6.7) | (45.8) |
| 43 | 1.55 | 50.8 | 7.4 | 41.8 |
| | | (51.0) | (7.2) | (41.8) |
| 44 | 1.62 | 46.9 | 6.5 | 46.6 |
| | | (47.5) | (6.5) | (46.0) |
| 45 | 1.65 | 49.2 | 6.9 | 43.9 |
| | | (49.3) | (6.9) | (43.8) |
| 46 | 2.08 | 49.6 | 7.3 | 43.1 |
| | | (50.0) | (7.2) | (42.8) |
| 47 | 2.03 | 49.5 | 7.3 | 43.2 |
| | | (50.0) | (7.2) | (42.8) |
| 48 | 1.88 | 48.0 | 6.9 | 45.1 |
| | | (48.4) | (6.9) | (44.7) |

The homopolymers obtained in Examples 35 to 48 are soluble in water, DMSO and DMF and insoluble in other organic solvents.

EXAMPLE 49

A 7.0 g quantity of glucosyloxyethyl methacrylate (HEMA-Glc) and 13.0 g of methyl methacrylate were dissolved in 70 ml of DMSO. A 25 mg quantity of AIBN was added to the obtained solution and the mixture was reacted with stirring at 65° C. for 10 hours in a nitrogen stream. After completion of the reaction, the highly viscous reaction mixture was diluted with 70 ml of DMSO and poured into 2 l of acetone to give a solution from which a copolymer was precipitated. The precipitate was purified by reprecipitation, giving 18.8 g of a white powder of copolymer (yield 94%).

The polymer swelled in water, greatly swelled in acetone, dissolved in acetone/water mixtures (9/1 and 8/2) and dissolved in DMSO.

Infrared absorption spectrum analysis reveals that peaks were found at 1440 (—COOCH$_3$) and at 980, 830 and 740 (all due to methyl methacrylate) in addition to the same peaks as observed in the analysis of the homopolymer obtained in Example 35.

When a film formed from this copolymer was immersed in water, the film held water in an amount corresponding to 58.1% of the weight of the copolymer and changed to a transparent film outstanding in strength and flexibility.

EXAMPLE 50

A 12.0 g quantity of glucosyloxyethyl methacrylate (HEMA-Glc), 8.0 g of methyl methacrylate, 40 ml of ethyl cellosolve, 16 ml of isopropanol and 14 ml of water were mixed together. To the mixture was added 30 mg of AIBN and the obtained mixture was reacted with stirring at 65° C. for 8 hours in a nitrogen stream. After completion of the reaction, the reaction mixture was purified in the same manner as in Example 49, giving 17.9 g of a copolymer as a white powder (yield 89.5%).

The thus obtained copolymer greatly swelled in water, slightly swelled in acetone, swelled in an acetone/water (9/1) mixture, dissolved in an acetone/water (8/2) mixture and dissolved in DMSO.

The copolymer showed the same infrared absorption spectrum as observed in the analysis of the copolymer obtained in Example 49.

When immersed in water, this copolymer changed to a soft gel containing water in an amount corresponding to 227% of the weight of the copolymer.

EXAMPLE 51

A 12.0 g quantity of galactosyloxyethyl acrylate (HEA-Gal), 8.0 g of styrene, 40 ml of ethyl cellosolve, 16 ml of isopropanol and 14 ml of water were mixed together. The mixture was treated by the same procedure as in Example 50, giving 15.2 g of a copolymer as a white powder (yield 76%).

The polymer swelled in water, did not swelled in acetone, greatly swelled in an acetone/water (9/1) mixture, greatly swelled in an acetone/water (8/2) mixture and dissolved in DMSO and in ethyl cellosolve.

The polymer showed absorptions at 1610, 1500, 1450 and 750 all due to the benzene ring in addition to the same infrared absorptions as observed in the analysis of the homopolymer obtained in Example 48.

EXAMPLE 52

In 80 ml of DMSO were dissolved 10 g of galactosyloxyethyl methacrylate (HEMA-Gal) and 10 g of acrylonitrile. Thirty milligrams of AIBM was added to the obtained solution and the mixture was reacted with stirring at 70° C. for 12 hours in a nitrogen stream, giving a pale yellow, transparent viscous liquid. The obtained liquid was diluted with 80 ml of DMSO and the diluted liquid was poured into 2 l of acetone to give a solution from which a copolymer was prepared. The precipitate was purified by reprecipitation, giving 17.8 g of a white powder of copolymer (yield 89%).

The polymer swelled in water, swelled in acetone, greatly swelled in an acetone/water (8/2) mixture, dissolved in DMSO and was insoluble in ethyl cellosolve.

The polymer showed sharp peaks at 2170 (—C N) and 1430 (—CH$_2$—CN) in addition to the same infrared absorptions as observed in the analysis of the homopolymer obtained in Example 48.

EXAMPLES 53 TO 88

Copolymers were prepared by the same reactions as conducted in Examples 49 to 52 except under the conditions as shown below in Table 4. All the obtained copolymers were soluble in DMSO and DMF, and those obtained in Examples 57, 58, 60 and 83 to 86 were soluble also in water.

In Table 4 below, Note 1) indicates a solvent mixture of 40 ml of ethyl cellosolve, 16 ml of isopropanol and 14 ml of water.

TABLE 4

| Example No. | Monomers used Kind | (g) | Solvent (Amount, ml) | Initiator (Amount, mg) | Temperature (°C.) | Time (hr) | Yield (g) | (%) |
|---|---|---|---|---|---|---|---|---|
| 53 | HEMA-Glc | 8.0 | Note 1) | AIBN | 65 | 8 | 17.5 | 87.5 |
|  | Styrene | 12.0 | (70) | (30) |  |  |  |  |
| 54 | HEMA-Glc | 12.0 | DMSO | AIBN | 65 | 8 | 15.8 | 79.0 |
|  | Styrene | 8.0 | (70) | (30) |  |  |  |  |
| 55 | HEMA-Glc | 8.0 | DMSO | AIBN | 65 | 8 | 17.9 | 89.5 |
|  | Acrylonitrile | 12.0 | (80) | (30) |  |  |  |  |
| 56 | HEMA-Glc | 12.0 | DMSO | AIBN | 65 | 8 | 18.2 | 91.0 |
|  | Acrylonitrile | 8.0 | (80) | (30) |  |  |  |  |
| 57 | HEMA-Glc | 8.0 | DMSO | AIBN | 70 | 10 | 16.2 | 81.0 |
|  | Acrylamide | 12.0 | (70) | (35) |  |  |  |  |
| 58 | HEMA-Glc | 12.0 | DMSO | AIBN | 70 | 10 | 17.5 | 87.5 |
|  | Acrylamide | 8.0 | (70) | (35) |  |  |  |  |
| 59 | HEMA-Glc | 10.0 | DMSO | AIBN | 65 | 10 | 16.5 | 82.5 |
|  | 2-Hydroxyethyl methacrylate | 10.0 | (70) | (30) |  |  |  |  |
| 60 | HEMA-Glc | 15.0 | Water | APS | 50 | 10 | 15.2 | 76.0 |
|  | Methacrylic acid | 5.0 | (70) | (40) |  |  |  |  |
| 61 | HEMA-Gal | 8.0 | DMSO | AIBN | 65 | 8 | 18.2 | 91.0 |
|  | Methyl methacrylate | 12.0 | (70) | (30) |  |  |  |  |
| 62 | HEMA-Gal | 12.0 | DMSO | AIBN | 65 | 8 | 17.9 | 89.5 |
|  | Methyl methacrylate | 8.0 | (70) | (30) |  |  |  |  |
| 63 | HEMA-Gal | 12.0 | Note 1) | AIBN | 65 | 8 | 16.5 | 82.5 |
|  | Styrene | 8.0 | (70) | (30) |  |  |  |  |
| 64 | HEMA-Gal | 10.0 | DMSO | AIBN | 65 | 8 | 15.8 | 79.0 |
|  | 2-Hydroxyethyl methacrylate | 10.0 | (70) | (30) |  |  |  |  |
| 65 | HEMA-Man | 10.0 | DMSO | AIBN | 65 | 8 | 18.0 | 90.0 |
|  | Methyl methacrylate | 10.0 | (70) | (30) |  |  |  |  |
| 66 | HEMA-Xyl | 10.0 | DMSO | AIBN | 65 | 8 | 17.8 | 89.0 |
|  | Methyl methacrylate | 10.0 | (80) | (30) |  |  |  |  |
| 67 | HEMA-Mal | 10.0 | DMSO | AIBN | 65 | 8 | 18.5 | 92.5 |
|  | Acrylonitrile | 10.0 | (80) | (30) |  |  |  |  |
| 68 | HEMA-Lac | 10.0 | DMSO | AIBN | 65 | 8 | 18.3 | 91.5 |
|  | Acrylonitrile | 10.0 | (80) | (30) |  |  |  |  |
| 69 | HPMA-Glc | 10.0 | DMSO | AIBN | 65 | 8 | 17.6 | 88.0 |
|  | Methyl methacrylate | 10.0 | (70) | (30) |  |  |  |  |
| 70 | HPMA-Glc | 10.0 | DMSO | AIBN | 65 | 8 | 18.8 | 94.0 |
|  | Acrylonitrile | 10.0 | (70) | (30) |  |  |  |  |
| 71 | HEA-Glc | 10.0 | DMSO | AIBN | 65 | 8 | 18.5 | 92.5 |
|  | Methyl methacrylate | 10.0 | (70) | (30) |  |  |  |  |

TABLE 4-continued

| Example No. | Monomers used Kind | (g) | Solvent (Amount, ml) | Initiator (Amount, mg) | Temperature (°C.) | Time (hr) | Yield (g) | (%) |
|---|---|---|---|---|---|---|---|---|
| 72 | HEA-Glc | 10.0 | DMSO | AIBN | 65 | 8 | 18.9 | 94.5 |
|  | Acrylonitrile | 10.0 | (70) | (30) |  |  |  |  |
| 73 | HEA-Gal | 10.0 | DMSO | AIBN | 65 | 8 | 18.2 | 91.0 |
|  | Methyl methacrylate | 10.0 | (70) | (30) |  |  |  |  |
| 74 | HEA-Gal | 10.0 | DMSO | AIBN | 65 | 8 | 17.9 | 89.5 |
|  | Acrylonitrile | 10.0 | (70) | (30) |  |  |  |  |
| 75 | HPA-Glc | 10.0 | DMSO | AIBN | 65 | 8 | 18.1 | 90.5 |
|  | Methyl methacrylate | 10.0 | (70) | (30) |  |  |  |  |
| 76 | HEEMA-Glc | 10.0 | DMSO | AIBN | 65 | 8 | 18.3 | 91.5 |
|  | Methyl methacrylate | 10.0 | (80) | (30) |  |  |  |  |
| 77 | HEEMA-Glc | 15.0 | Note 1) | AIBN | 65 | 8 | 16.7 | 83.5 |
|  | Styrene | 5.0 | (70) | (30) |  |  |  |  |
| 78 | HEEMA-Glc | 10.0 | DMSO | AIBN | 65 | 8 | 18.0 | 90.0 |
|  | Acrylonitrile | 10.0 | (80) | (30) |  |  |  |  |
| 79 | HEEMA-Gal | 10.0 | DMSO | AIBN | 65 | 8 | 17.8 | 89.0 |
|  | Methyl methacrylate | 10.0 | (80) | (30) |  |  |  |  |
| 80 | HEEMA-Gal | 10.0 | DMSO | AIBN | 65 | 8 | 18.2 | 91.0 |
|  | Acrylonitrile | 10.0 | (80) | (30) |  |  |  |  |
| 81 | HEEA-Glc | 10.0 | DMSO | AIBN | 65 | 8 | 18.2 | 91.0 |
|  | Methyl methacrylate | 10.0 | (80) | (30) |  |  |  |  |
| 82 | HEEA-Glc | 10.0 | DMSO | AIBN | 65 | 8 | 18.7 | 93.5 |
|  | Acrylonitrile | 10.0 | (80) | (30) |  |  |  |  |
| 83 | HEMA-Glc | 10.0 | Water | APS | 50 | 10 | 19.2 | 96.0 |
|  | HEMA-Gal | 10.0 | (80) | (40) |  |  |  |  |
| 84 | HEMA-Glc | 10.0 | Water | APS | 50 | 10 | 18.9 | 94.5 |
|  | HEA-Glc | 10.0 | (80) | (40) |  |  |  |  |
| 85 | HEMA-Glc | 10.0 | Water | APS | 50 | 10 | 19.3 | 96.5 |
|  | HEMA-Xyl | 10.0 | (80) | (40) |  |  |  |  |
| 86 | HEMA-Glc | 10.0 | Water | APS | 50 | 10 | 19.1 | 95.5 |
|  | HEEMA-Glc | 10.0 | (80) | (40) |  |  |  |  |
| 87 | HEEMA-Glc3 | 7.0 | DMSO | AIBN | 65 | 10 | 17.6 | 88.0 |
|  | Methyl methacrylate | 13.0 | (70) | (25) |  |  |  |  |
| 88 | HEEMA-Glc3 | 12.0 | DMSO | AIBN | 65 | 10 | 16.8 | 84.0 |
|  | Methyl methacrylate | 8.0 | (70) | (25) |  |  |  |  |

Table 5 below shows the intrinsic viscosity (in DMSO, at 25° C.), ratio of the copolymerized monomers and the results of elementary analysis, with respect to the copolymers obtained above.

The ratio of the copolymerized monomers was determined by the "sugar analysis", "elementary analysis" and "other methods" as described below.

Sugar analysis

A 50 mg quantity of the copolymer was dispersed or dissolved in 10 ml of a 2N aqueous solution of hydrochloric acid to undergo hydrolysis at 95° to 100° C. for 6 hours. After completion of the reaction, the precipitate was filtered off and the sugar in the filtrate was quantitatively determined according to the phenolsulfuric acid method.

Elementary analysis

In respect of copolymers containing a nitrogen-containing monomer, the ratio of the copolymerized monomers was determined from the nitrogen content obtained by elementary analysis, whereas as to styrene-containing copolymers, the ratio thereof was determined from the carbon content obtained by elementary analysis.

Other methods

Example 83: The ratio of constituent monomers was determined from the results of quantitative determination of sugar in the foregoing sugar analysis, quantitative determination of sugar by liquid chromatography and quantitative determination of glucose thereby.

Liquid chromatography:

The same filtrate as obtained after hydrolysis in the sugar analysis was subjected to liquid chromatography under the following conditions:

Column: TSKgel Amide-80
Eluent: a 75/25 mixture of acetonitrile/water
Flow rate: 1.0 ml/min
Detector: differential refractive index detector (RI)

Determination of glucose:

The same filtrate as obtained after hydrolysis in the sugar analysis was subjected to colorimetric determination with use of a kit for determination of glucose (trade name: Glucose B-test kit, manufactured by Wako Pure Chemicals, Inc.).

Example 84: The ratio of the copolymerized monomers was determined from the results of sugar analysis and elementary analysis and was confirmed by $^1$H-NMR.

$^1$H-NMR:

Conducted in heavy water and determined from the following peak. 0.8–1.3 ppm (broad peak due to CH$_3$ group)

Example 85: Determined from the results of the quantitative analysis of the sugar constituents by liquid chromatography.

Example 86: The ratio of the copolymerized monomers was determined from the results of sugar analysis and elementary analysis and was confirmed by $^{13}$C-NMR.

$^{13}$C-NMR: Conducted in heavy water and determined from the following peaks. 66.1–63.7 ppm (several sharp peaks due to CH$_2$ in ethylene moiety)

(Note: In Table 5, the term "copolymerization ratio" means the ratio of the copolymerized monomers.)

TABLE 5

| Example No. | Constituent monomers Kind | Ratio (mol %) | Method for determining copolymerization ratio | Intrinsic viscosity | Elementary analysis (Calcd.) C | H | N |
|---|---|---|---|---|---|---|---|
| 49 | HEMA-Glc | 14.4 | Sugar analysis | 1.93 | 54.0 | 6.7 | 0.0 |
| | Methyl methacrylate | 85.6 | | | (54.1) | (6.6) | (0.0) |
| 50 | HEMA-Glc | 34.6 | Sugar analysis | 0.52 | 51.4 | 6.7 | 0.0 |
| | Methyl methacrylate | 65.4 | | | (51.4) | (6.8) | (0.0) |
| 51 | HEA-Gal | 41.1 | Elementary analysis | 0.48 | 55.0 | 6.7 | 0.0 |
| | Styrene | 58.6 | | | (55.0) | (6.7) | (0.0) |
| 52 | HEMA-Gal | 16.0 | Elementary analysis | 2.08 | 52.1 | 6.7 | 3.9 |
| | Acrylonitrile | 84.0 | | | (52.1) | (6.7) | (3.9) |
| 53 | HEMA-Glc | 19.1 | Elementary analysis | 0.60 | 64.3 | 7.2 | 0.0 |
| | Styrene | 80.9 | | | (64.3) | (7.2) | (0.0) |
| 54 | HEMA-Glc | 38.2 | Elementary analysis | 0.80 | 56.6 | 7.0 | 0.0 |
| | Styrene | 61.8 | | | (56.6) | (7.0) | (0.0) |
| 55 | HEMA-Glc | 10.3 | Elementary analysis | 2.10 | 53.5 | 6.6 | 5.9 |
| | Acrylonitrile | 89.7 | | | (53.5) | (6.6) | (5.9) |
| 56 | HEMA-Glc | 21.5 | Elementary analysis | 2.50 | 51.3 | 6.8 | 2.8 |
| | Acrylonitrile | 78.5 | | | (51.3) | (6.8) | (2.8) |
| 57 | HEMA-Glc | 16.3 | Elementary analysis | 2.72 | 49.6 | 6.9 | 4.6 |
| | Acrylamide | 83.7 | | | (49.6) | (6.9) | (4.6) |
| 58 | HEMA-Glc | 30.2 | Elemantary analysis | 2.90 | 49.5 | 6.9 | 2.4 |
| | Acrylamide | 69.8 | | | (49.5) | (6.9) | (2.4) |
| 59 | HEMA-Glc | 35.3 | Sugar analysis | 3.43 | 50.8 | 7.2 | 0.0 |
| | 2-Hydroxyethyl methacrylate | 64.7 | | | (50.9) | (7.1) | (0.0) |
| 60 | HEMA-Glc | 50.4 | Sugar analysis | 3.21 | 49.2 | 6.8 | 0.0 |
| | Methacrylic acid | 49.6 | | | (49.9) | (6.7) | (0.0) |
| 61 | HEMA-Gal | 18.4 | Sugar analysis | 1.85 | 53.0 | 6.7 | 0.0 |
| | Methyl methacrylate | 81.6 | | | (53.3) | (6.7) | (0.0) |
| 62 | HEMA-Gal | 33.4 | Sugar analysis | 1.96 | 51.1 | 6.8 | 0.0 |
| | Methyl methacrylate | 66.6 | | | (51.5) | (6.8) | (0.0) |
| 63 | HEMA-Gal | 39.8 | Elementary analysis | 0.73 | 56.2 | 7.0 | 0.0 |
| | Styrene | 60.2 | | | (56.2) | (7.0) | (0.0) |
| 64 | HEMA-Gal | 32.6 | Sugar analysis | 3.32 | 50.8 | 7.2 | 0.0 |
| | 2-Hydroxyethyl methacrylate | 67.4 | | | (51.1) | (7.1) | (0.0) |
| 65 | HEMA-Man | 25.0 | Sugar analysis | 1.94 | 52.0 | 6.7 | 0.0 |
| | Methyl methacrylate | 75.0 | | | (52.3) | (6.7) | (0.0) |
| 66 | HEMA-Xyl | 27.6 | Sugar analysis | 1.16 | 53.0 | 6.8 | 0.0 |
| | Methyl methacrylate | 72.4 | | | (53.3) | (6.7) | (0.0) |
| 67 | HEMA-Mal | 10.1 | Elementary analysis | 3.31 | 49.8 | 6.6 | 2.9 |
| | Acrylonitrile | 89.9 | | | (49.8) | (6.6) | (2.9) |
| 68 | HEMA-Lac | 10.0 | Elementary analysis | 3.29 | 49.8 | 6.6 | 2.9 |
| | Acrylonitrile | 90.0 | | | (49.8) | (6.6) | (2.9) |
| 69 | HPMA-Glc | 23.5 | Sugar analysis | 1.82 | 53.1 | 7.0 | 0.0 |
| | Methyl methacrylate | 76.5 | | | (53.5) | (7.0) | (0.0) |
| 70 | HPMA-Glc | 14.6 | Elementary analysis | 2.87 | 53.5 | 7.0 | 3.9 |
| | Acrylonitrile | 85.4 | | | (53.5) | (7.0) | (3.9) |
| 71 | HEA-Glc | 25.1 | Sugar analysis | 1.64 | 50.9 | 6.4 | 0.0 |
| | Methyl methacrylate | 74.9 | | | (51.2) | (6.4) | (0.0) |
| 72 | HEA-Glc | 15.8 | Elementary analysis | 2.75 | 50.8 | 6.4 | 4.3 |
| | Acrylonitrile | 84.2 | | | (50.8) | (6.4) | (4.3) |
| 73 | HEA-Gal | 26.1 | Sugar analysis | 1.77 | 50.7 | 6.5 | 0.0 |
| | Methyl methacrylate | 73.9 | | | (51.1) | (6.4) | (0.0) |
| 74 | HEA-Gal | 16.0 | Elementary analysis | 2.80 | 50.8 | 6.3 | 4.2 |
| | Acrylonitrile | 84.0 | | | (50.8) | (6.3) | (4.2) |
| 75 | HPA-Glc | 24.9 | Sugar analysis | 1.68 | 52.1 | 6.8 | 0.0 |
| | Methyl methacrylate | 75.1 | | | (52.3) | (6.7) | (0.0) |
| 76 | HEEMA-Glc | 22.4 | Sugar analysis | 2.43 | 52.2 | 7.0 | 0.0 |
| | Methyl | 77.6 | | | (52.6) | (7.0) | (0.0) |

TABLE 5-continued

| Example No. | Constituent monomers Kind | Ratio (mol %) | Method for determining copolymerization ratio | Intrinsic viscosity | Elementary analysis (Calcd.) C | H | N |
|---|---|---|---|---|---|---|---|
| | methacrylate | | | | | | |
| 77 | HEEMA-Glc | 54.6 | Elementary | 2.58 | 53.1 | 7.2 | 0.0 |
| | Styrene | 45.4 | analysis | | (53.1) | (7.2) | (0.0) |
| 78 | HEEMA-Glc | 13.5 | Elementary | 3.43 | 52.5 | 7.0 | 3.6 |
| | Acrylonitrile | 86.5 | analysis | | (52.5) | (7.0) | (0.0) |
| 79 | HEEMA-Gal | 22.9 | Sugar analysis | 2.04 | 52.3 | 7.0 | 0.0 |
| | Methyl methacrylate | 77.1 | | | (52.5) | (7.0) | (0.0) |
| 80 | HEEMA-Gal | 13.4 | Elementary | 4.02 | 52.5 | 7.0 | 3.7 |
| | Acrylonitrile | 86.6 | analysis | | (52.5) | (7.0) | (3.7) |
| 81 | HEEA-Glc | 23.3 | Sugar analysis | 3.86 | 51.1 | 6.8 | 0.0 |
| | Methyl methacrylate | 76.7 | | | (51.4) | (6.7) | (0.0) |
| 82 | HEEA-Glc | 13.9 | Elementary | 4.03 | 51.2 | 6.7 | 3.8 |
| | Acrylonitrile | 86.1 | analysis | | (51.2) | (6.7) | (3.8) |
| 83 | HEMA-Glc | 50.2 | Other method | 1.96 | 49.2 | 6.9 | 0.0 |
| | HEMA-Gal | 49.8 | | | (49.3) | (6.9) | (0.0) |
| 84 | HEMA-Glc | 48.5 | Other method | 2.43 | 48.2 | 6.7 | 0.0 |
| | HEA-Glc | 51.5 | | | (48.4) | (6.7) | (0.0) |
| 85 | HEMA-Glc | 47.2 | Other method | 1.75 | 49.7 | 6.9 | 0.0 |
| | HEMA-Xyl | 52.8 | | | (49.8) | (6.9) | (0.0) |
| 86 | HEMA-Glc | 54.3 | Other method | 4.03 | 49.5 | 7.1 | 0.0 |
| | HEEMA-Glc | 45.7 | | | (49.7) | (7.1) | (0.0) |
| 87 | HEEMA-Glc3 | 7.9 | Sugar analysis | 2.01 | 49.5 | 6.5 | 0.0 |
| | Methyl methacrylate | 92.1 | | | (50.0) | (6.5) | (0.0) |
| 88 | HEEMA-Glc3 | 19.4 | Sugar analysis | 0.75 | 47.5 | 6.6 | 0.0 |
| | Methyl methacrylate | 80.6 | | | (48.1) | (6.5) | (0.0) |

EXAMPLE 89

Six grams of glucosyloxyethyl methacrylate (HEMA-Glc), 4 g of methyl methacrylate and 10 g of methacrylic acid were dissolved in a solvent mixture of 105 ml of isopropanol (IPA) and 35 ml of water. Thirty milligrams of AIBN was added to the obtained solution and the mixture was reacted with stirring at 65° C. for 8 hours in a nitrogen stream. After completion of the reaction, the reaction mixture was diluted with 30 mg of IPA and the diluted mixture was poured into 2 l of hexane to give a solution from which a copolymer was precipitated. The precipitate was purified by reprecipitation, giving 18.5 g of a white powder of copolymer (yield 92.5%). The intrinsic viscosity [η] of the obtained polymer was 0.82 (in DMF, 25° C.). The polymer was soluble in a water/IPA (9/1) mixture, a water/IPA/toluene (1/8/2) mixture, ethyl cellosolve, DMSO and DMF.

EXAMPLE 90

Polystyrene beads (150 μm in diameter) were immersed in solutions of 2 wt % of each of the polymers 1 to 8 as shown below in Table 6 in a dioxane/water mixture (the ratio of dioxane to water was changed according to the solubility of the polymer). The superfluous solution was filtered off and the beads were dried at 100° C. and further vacuum dried at 80° C. for 10 hours, giving polystyrene beads coated with each polymer (film thickness: 2 to 3 μm).

Since the polymers 1 and 2 were soluble in water, p-toluenesulfonic acid was added to the solution in an amount corresponding to 0.3% of the weight of the polymer and the obtained mixture was heated to 100° C. to cause the crosslinking of hydoxyl groups on the sugar residue before coating the beads. After the crosslinking, the reaction mixture was immersed in water to remove the catalyst.

A platelet-rich plasma collected by centrifuging the citrated blood of a rabbit was adjusted to a final concentration to a hundred thousand cells/μl. At room temperature, the plasma was loaded into a Teflon column containing the polystyrene beads coated with each polymer. From the number of platelets measured before and after the loading, the percentage of platelets adhering to the beads (percentage of adhesion of platelets, %) was determined. Table 6 shows the results.

TABLE 6

| Specimen | Ratio of adhesion of platelets (%) |
|---|---|
| Uncoated | 97.0 |
| Polymer-1 (Ex. 35) | 8.2 |
| Polymer-2 (Ex. 36) | 7.6 |
| Polymer-3 (Ex. 49) | 12.3 |
| Polymer-4 (Ex. 50) | 5.2 |
| Polymer-5 (Ex. 51) | 7.5 |
| Polymer-6 (Ex. 38) | 7.3 |
| Polymer-7 (Ex. 87) | 10.8 |
| Polymer-8 (Ex. 88) | 7.5 |

Table 6 reveals that only a very small quantity of platelets remained adhered to the surface of the material of the invention.

EXAMPLE 91

A suspension of platelets of a rabbit ($3 \times 10^8$ pieces/ml) having loaded therein a fluorescent coloring matter Furo2-AM capable of bonding to $Ca^{2+}$ was poured into a Teflon column containing the polystyrene beads coated with each of the polymers 1 to 8 by the same procedure as in Example 1. The concentration of $Ca^{2+}$ in the platelets eluted out of the Teflon column was measured with use of a calcimeter. Table 2 below shows the incremental amount of the concentration (nM) of $Ca^{2+}$ before and after charging the suspension into the column.

TABLE 7

| Specimen | Incremental amount of Ca$^{2+}$ concentration (nM) |
| --- | --- |
| Uncoated | 420 |
| Polymer-1 | 130 |
| Polymer-2 | 125 |
| Polymer-3 | 158 |
| Polymer-4 | 93 |
| Polymer-5 | 112 |
| Polymer-6 | 108 |
| Polymer-7 | 144 |
| Polymer-8 | 90 |

Table 7 shows that the platelets contacted with the material of the invention are unlikely to become active and that the material of the invention has a very high compatibility with blood.

EXAMPLES 92 TO 110

The polymers 1 to 8 of the invention used in Examples 90 and 91 and the polymer-9 of the invention prepared in Example 89 were each admixed with the additives as shown below in Table 8 in the listed amounts (by weight), giving the compositions of the invention having a solids content of 20%.

A silicone oligomer, i.e. a hydrolyzate of silicone, to be used as the additives was prepared by adding dropwise 6.9 g of a 0.02N aqueous solution of hydrochloric acid to 30 g of γ-glycidoxypropyl-trimetoxysilane with stirring and allowing the resulting mixture to age by standing overnight.

COMPARISON EXAMPLES 1 TO 4

The following 2-HEMA-containing copolymer (polymer-10) was mixed with the additives as shown in Table 8 in the listed amounts (by weight), giving a comparative composition having a solids content of 20%.

Synthesis of 2-HEMA-containing copolymer:

A 12 g quantity of 2-hydroxyethyl methacrylate and 8 g of methyl methacrylate were dissolved in a solvent mixture of 40 ml of ethyl cellosolve, 16 ml of IPA and 40 ml of water. Thirty milligrams of AIBN was added to the obtained solution and the mixture was reacted with stirring at 65° C. for 8 hours in a nitrogen stream. After completion of the reaction, the reaction mixture was diluted with 70 ml of IPA and the diluted mixture was poured into 2 l of hexane to give a solution from which a copolymer was precipitated. The precipitate was purified by reprecipitation, giving 18.2 g of a white powder of copolymer (yield 91%). This copolymer will be hereinafter referred to as "polymer-10". The intrinsic viscosity [η] of the polymer was 0.50 (in DMF, 25° C.).

The solvent used in Examples 1 to 4 was a mixture of methanol/IPA/water/DMF (=45/30/15/10, ratio by volume, ml). The solvent used in the other Examples and Comparison Examples was a mixture of methanol/IPA/water/carbitol acetate (=45/30/15/10, ratio by volume, ml).

TABLE 8

| | Example | | | | | | | | | | | |
| --- | --- | --- | --- | --- | --- | --- | --- | --- | --- | --- | --- | --- |
| | 92 | 93 | 94 | 95 | 96 | 97 | 98 | 99 | 100 | 101 | 102 | 103 |
| Polymer | | | | | | | | | | | | |
| No. | 1 | 1 | 2 | 2 | 3 | 3 | 4 | 4 | 9 | 9 | 9 | 9 |
| Amount | 100 | 100 | 100 | 100 | 100 | 100 | 100 | 100 | 100 | 100 | 100 | 100 |
| Sorbitol poly-glycidyl ether | 70 | 70 | 70 | 70 | 20 | 20 | 20 | 20 | 20 | 20 | | |
| Methylated melamine resin | | | | | | | | | | | 20 | 20 |
| Silicone oligomer | | | | | | | | | | | | |
| 1,8-Diaza-bicyclo(5.4.0)undecene-7 | 1 | 1 | 1 | 1 | 1 | 1 | 1 | 1 | 1 | 1 | | |
| p-Toluene-sulfonic acid | | | | | | | | | | | 1 | 1 |
| Dodecylglucoside | | 10 | | 10 | | 10 | | 10 | | 10 | | |
| Polyoxyethylene nonyl phenyl ether | | | | | | | | | | | | |

| | Example | | | | | | | Comp. Example | | | |
| --- | --- | --- | --- | --- | --- | --- | --- | --- | --- | --- | --- |
| | 104 | 105 | 106 | 107 | 108 | 109 | 110 | 1 | 2 | 3 | 4 |
| Polymer | | | | | | | | | | | |
| No. | 9 | 9 | 9 | 5 | 6 | 7 | 8 | 10 | 10 | 10 | 10 |
| Amount | 100 | 100 | 100 | 100 | 100 | 100 | 100 | 100 | 100 | 100 | 100 |
| Sorbitol poly-glycidyl ether | | | | 20 | 70 | 20 | 20 | 20 | 20 | | |
| Methylated melamine resin | 20 | | | | | | | | | 20 | 20 |
| Silicone oligomer | | 40 | 40 | | | | | | | | |
| 1,8-Diaza-bicyclo(5,4,0)undecene-7 | | 1.5 | 1.5 | 1 | 1 | 1 | 1 | 1 | 1 | | |
| p-Toluene-sulfonic acid | 1 | | | | | | | | | 1 | 1 |
| Dodecylglucoside | | | | | | | | | | | |
| Polyoxyethylene nonyl phenyl ether | 10 | | 10 | 10 | 10 | 10 | 10 | | 10 | | 10 |

The additives listed in Table 8 are sorbitol polyglycidyl ether (trade name: DENACOL EX-614, product of Nagase Kasei Kogyo Co., Ltd.), methylated melamine resin (tade name: Sumimal M-55, product of Sumitomo Chemical Co., Ltd.) and 1,8-diazabicyclo(5,4,0)undecene-7 (product of SAN-APPRO Ltd.).

The obtained composition was applied to a 2 mm-thick plate made of a polycarbonate (trade name: POLYCACE, product of Tsutsunaka Plastic Industry Co., Ltd.) to a dry film thickness of 8 to 12 μm. The coated plate was cured by heating at 120° C. for 1 hour.

The following tests were carried out using as a specimen the thus obtained polycarbonate plate coated with a non-fogging, drip-proof film. Table 9 shows the results.

Figure 9:
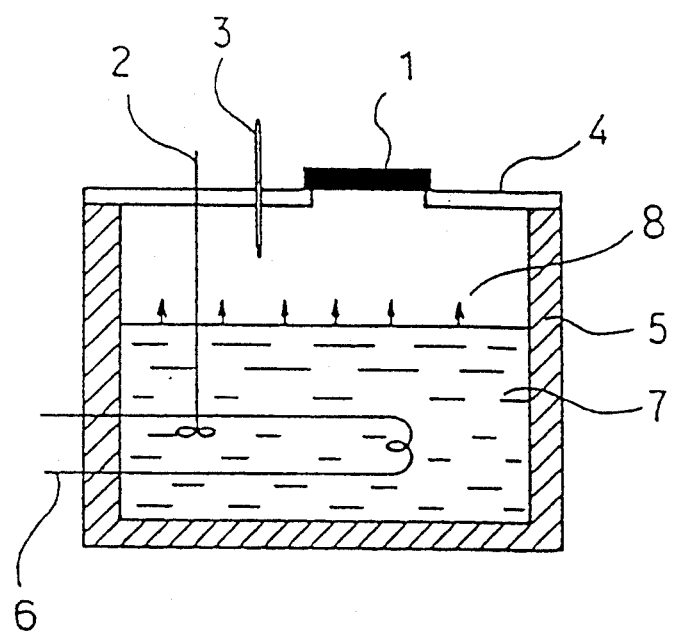
FIG. 9 shows the apparatus to check the specimens for the Non-fogging and drip-proof-properties. The reference characters designate: 1. a specimen; 2. a stirring rod (blade); 3. thermometer; 4. a cover; 5. heat-insulating vessel; 6. heater; 7. warm water (40° C.); and 8. steam.

Non-fogging and drip-proof properties:

The apparatus as illustrated in FIG. 9 was used to check the specimens for the non-fogging and drip-proof properties. In FIG. 9, the reference characters designate: 1, a specimen; 2, a stirring rod (blade); 3, thermometer; 4, a cover; 5, heat-insulating vessel; 6, heater; 7, warm water (40° C.); and 8, steam. The specimen was placed at the specified position in the apparatus, and the time taken until the occurrence of fogging on the specimen was measured. The degrees of non-fogging and drip-proof properties were evaluated according to the following criteria.

A: One minute or longer. Very satisfactory in non-fogging property.

B: 30 to 60 seconds. Satisfactory in non-fogging property.

C: 10 to 30 seconds. Insufficient in non-fogging property.

D: Up to 10 seconds. Poor in non-fogging property.

Contact angle:

In a room at 25° C., the contact angle of the coating was measured while pouring 1 ml of pure water over the specimen with capillaries. Specimens having a contact angle of up to 5° were indicated with the mark "A".

Surface hardness:

The specimen was rubbed with a mat of steel wool #0000 (load: 5 g/cm$^2$), and the degree of scratching detected on the coating was evaluated according to the following criteria.

A: No mar was detected on the specimen.

B: The specimen sustained 1 or 2 scratches but with no problem.

C: The specimen sustained 5 to 10 scratches but with no problem.

D: More than 10 scratches were detected on the specimen.

Water resistance:

The specimen was immersed in water at 25° C. for 12 hours, and the appearance of the coating was evaluated according to the following criteria.

A: No change.

B: The coating slightly swelled, but returned to the original state before immersion when left to stand.

C: The coating significantly swelled and did not return to the original state when left to stand.

D: The coating peeled from the specimen during the immersion in water.

The degree of fogging on the coating was evaluated according to the same criteria as above.

Resistance to hot water:

The specimen was immersed in hot water at 80° C. for 30 minutes, and the appearance of the coating was evaluated according to the same criteria as in the water resistance test.

The degree of fogging of the coating was evaluated according to the same criteria as above.

|  | Example |  |  |  |  |  |  |  |  |  |  |  |
|---|---|---|---|---|---|---|---|---|---|---|---|---|
|  | 92 | 93 | 94 | 95 | 96 | 97 | 98 | 99 | 100 | 101 | 102 | 103 |
| Non-fogging property | A | A | A | A | B | A | A | A | B | A | B | A |
| Contact angle | A | A | A | A | 38 | A | 35 | A | 37 | A | 41 | A |
| Surface hardness | B | B | B | B | B | B | B | B | B | B | A | A |
| Water resistance |  |  |  |  |  |  |  |  |  |  |  |  |
| Appearance | B | B | B | B | B | B | B | B | B | B | B | B |
| Non-fogging property | A | A | A | A | B | A | A | A | B | A | B | A |
| Resistance to hot water |  |  |  |  |  |  |  |  |  |  |  |  |
| Appearance | B | B | B | B | B | B | B | B | B | B | B | B |
| Non-fogging property | A | A | A | A | B | A | A | A | B | A | B | A |

|  | Example |  |  |  |  |  |  | Comp. Example |  |  |  |
|---|---|---|---|---|---|---|---|---|---|---|---|
|  | 104 | 105 | 106 | 107 | 108 | 109 | 110 | 1 | 2 | 3 | 4 |
| Non-fogging property | B | A | A | A | A | A | A | D | B | D | B |
| Contact angle | A | 30 | A | A | A | A | A | 51 | A | 55 | A |
| Surface hardness | A | A | A | B | B | B | B | C | C | C | C |
| Water resistance |  |  |  |  |  |  |  |  |  |  |  |
| Appearance | B | B | B | B | B | B | B | C | C | B | B |
| Non-fogging property | A | A | A | A | A | A | A | D | D | D | D |
| Resistance to hot water |  |  |  |  |  |  |  |  |  |  |  |
| Appearance | B | B | B | B | B | B | B | C | C | B | B |
| Non-fogging property | A | A | A | A | A | A | A | D | D | D | D |

Table 9 reveals that the cured coatings formed from the composition of the invention are excellent in non-fogging and drip-proof properties, substantially free of reduction in non-fogging and drip-proof properties even when exposed to water or hot water, very satisfactory in resistance to scratching, and well-balanced in the properties required of non-fogging and drip-proof coatings.

We claim:

1. A glycoside derivative-containing polymer having at least one of repeated units (I) represented by the formula

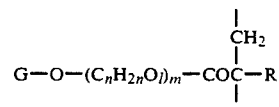

wherein G—O— is a saccharide residue having no protective group, R is a hydrogen atom or a methyl group, m is 1 or 2, n is an integer of 1 to 4, and l is an integer of 1 or more provided that $l \leq n$.

2. A polymer according to claim 1 which is a homopolymer having repeated units (I) or a copolymer having at least two different repeated units (I).

3. A polymer according to claim 2 which is a copolymer having repeated units (I) and repeated units copolymerizable therewith.

4. A polymer according to claim 3 wherein the copolymerizable repeated units are olefin-type repeated units.

5. A polymer according to claim 4 wherein the olefin-type repeated units are those represented by the formula

wherein $R^2$, $R^3$ and $R^4$ are the same or different and each represent a hydrogen atom or a methyl group, and $R^5$ is a group

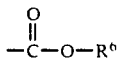

(wherein $R^6$ is a hydrogen atom, an alkyl group, a hydroxyalkyl group, a cycloalkyl group, an aminoalkyl group, a dialkylaminoalkyl group, a glycidyl group, a tetrahydrofuranyl group, a benzyl group, a group —$(CH_2CH_2O)_aCH_2CH_2OH$ (wherein a is an integer of 1 to 10), a group

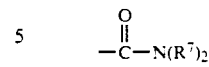

(wherein $R^7$ is a hydrogen atom or a lower alkyl group, provided that two groups $R^7$ are the same or different), a cyano group, a hydroxy group, a group

(wherein $R^8$ is a lower alkyl group), a phenyl group which may have at least one substituent selected from the group consisting of chlorine atom, lower alkyl group, cyano group, amino group, hydroxy group and lower alkoxy group, a pyridyl group optionally substituted with a lower alkyl group, a 2-oxypyrrolyl group optionally substituted with an alkyl group, or a carbazole group.

6. A polymer according to claim 3 wherein the copolymer has 1 to 99 mole % of repeated units (I) and 99 to 1 mole % of repeated units copolymerizable therewith.

7. A material compatible with blood which contains the glycoside derivative-containing polymer of claim 1.

8. A non-fogging drip-proof composition which contains the glycoside derivative-containing polymer of claim 1.

* * * * *